US008673866B2

(12) United States Patent
Wasan et al.

(10) Patent No.: US 8,673,866 B2
(45) Date of Patent: *Mar. 18, 2014

(54) STABILIZED FORMULATION FOR ORAL ADMINISTRATION OF THERAPEUTIC AGENTS AND RELATED METHODS

(75) Inventors: Kishor M. Wasan, Richmond (CA); Ellen K. Wasan, Richmond (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/456,023

(22) Filed: Apr. 25, 2012

(65) Prior Publication Data
US 2012/0270822 A1    Oct. 25, 2012

Related U.S. Application Data

(63) Continuation of application No. PCT/CA2010/001687, filed on Oct. 26, 2010.

(60) Provisional application No. 61/255,008, filed on Oct. 26, 2009, provisional application No. 61/365,708, filed on Jul. 19, 2010.

(51) Int. Cl.
    *A61K 31/70* (2006.01)
(52) U.S. Cl.
    USPC .......................................................... 514/31
(58) Field of Classification Search
    USPC .......................................................... 514/31
    See application file for complete search history.

(56) References Cited

U.S. PATENT DOCUMENTS

| 5,444,052 | A | 8/1995 | Pieringer | |
|---|---|---|---|---|
| 6,294,192 | B1 | 9/2001 | Patel | |
| 6,660,761 | B2 * | 12/2003 | Khanuja et al. | 514/396 |
| 6,770,290 | B1 * | 8/2004 | Proffitt et al. | 424/450 |
| 6,852,334 | B1 | 2/2005 | Cullis | |
| 6,923,988 | B2 | 8/2005 | Patel | |
| 7,053,061 | B2 | 5/2006 | Pai | |
| 7,060,285 | B2 | 6/2006 | Muller | |
| 7,326,691 | B2 | 2/2008 | Duddu | |
| 8,067,032 | B2 | 11/2011 | Chaubal | |
| 2004/0146538 | A1 | 7/2004 | Benameur | |
| 2005/0112188 | A1 | 5/2005 | Eliaz | |
| 2005/0191343 | A1 | 9/2005 | Liang | |
| 2008/0286373 | A1 | 11/2008 | Palepu | |

FOREIGN PATENT DOCUMENTS

| CA | 2 526 616 C | 9/2004 |
|---|---|---|
| CA | 2 604 943 A1 | 10/2006 |
| CN | 1897918 A | 1/2007 |
| EP | 1 170 003 A1 | 1/2002 |
| EP | 1 661 557 A1 | 5/2006 |
| EP | 1 328 254 B1 | 2/2007 |
| JP | 2003-252750 A | 9/2003 |
| JP | 2004-536144 A | 12/2004 |
| JP | 2007-512373 A | 5/2007 |
| WO | 95/08983 A1 | 4/1995 |
| WO | 02/34236 A2 | 5/2002 |
| WO | 03/093344 A1 | 11/2003 |
| WO | 2004/034992 A2 | 4/2004 |
| WO | 2004/050068 A1 | 6/2004 |
| WO | 2004/105694 A2 | 12/2004 |
| WO | 2005/048952 A2 | 6/2005 |
| WO | 2005/053612 A2 | 6/2005 |
| WO | 2006/113505 A2 | 10/2006 |
| WO | 2008/058234 A2 | 5/2008 |

OTHER PUBLICATIONS

Hauss et al, Journal of Pharmaceutical Sciences 87(2): 164-169, Feb. 1998.*
Bittner et al, Arzneim.-Forsch./Drug Res. 52, No. 9, 684-688 (2002).*
Collnot et al, Molecular Pharmaceutics, vol. 4, No. 3, 465-474 (2007).*
Amphotericin B: Instructions for use, contraindications, and the price of, <http://www.rlsnet.ru/tn_index_id_4172.htm> (retrieved Mar. 3, 2012), 5 pages.
Communication Pursuant to Article 94(3) EPC dated Jul. 17, 2013, issued in corresponding European Application No. 08 748 337.6, filed May 23, 2008, 7 pages.
Cruz, F.S., et al., "Prevention of Transfusion-Induced Chagas' Disease by Amphotericin B," American Journal of Tropical Medicine and Hygiene 29(5):761-765, Sep. 1980.
Deleers, M., and W.J. Malaisse, "Facilitated Fusion of Liposomes With Glycerol Monoleate Planar Bilayer," FEBS Letters 132(2):224-226, Sep. 1981.
Examination Report mailed Feb. 16, 2012, issued by the Hungarian Intellectual Property Office in corresponding Singapore Application No. 200907780-1, filed May 23, 2008, 8 pages.
Hauss, D.J., et al., "Lipid-Based Delivery Systems for Improving the Bioavailability and Lymphatic Transport of a Poorly Water-Soluble LTB4 Inhibitor," Journal of Pharmaceutical Sciences 87(2):164-169, Feb. 1998.
International Preliminary Report on Patentability mailed Feb. 20, 2012, issued in corresponding International Application No. PCT/CA2010/001687, filed Oct. 26, 2010, 6 pages.
International Search Report and Written Opinion mailed Sep. 29, 2008, issued in corresponding International Application No. PCT/CA2008/000975, filed May 23, 2008, 8 pages.
KarataŞ, A., et al., "Improved Solubility and Dissolution Rate of Piroxicam Using Gelucire 44/14 and Labrasol," Il Farmaco 60(9):777-782, Sep. 2005.
Notice of Reasons for Rejection mailed Feb. 18, 2013, issued in corresponding Japanese Application No. 2010-508677, filed May 23, 2008, 10 pages.
Notification of the Third Office Action, dated Jul. 29, 2013, issued in corresponding Chinese Application No. 200880023444.X, filed May 23, 2008, 10 pages.

(Continued)

*Primary Examiner* — Elli Peselev
(74) *Attorney, Agent, or Firm* — Christensen O'Connor Johnson Kindness PLLC

(57) ABSTRACT

Stable formulations for the oral administration of therapeutic agents, methods for administering therapeutic agents using the formulations, and methods for treating conditions and diseases using the formulations.

17 Claims, 11 Drawing Sheets

(56) References Cited

OTHER PUBLICATIONS

Risovic, V., et al., "Potential Mechanisms by Which Peceol® Increases the Gastrointestinal Absorption of Amphotericin B," Drug Development and Industrial Pharmacy 30(7):767-774, Aug. 2004.

Shah, N.H., et al., "Self-Emulsifying Drug Delivery Systems (SEDDS) With Polyglycolyzed Glycerides for Improving in Vitro Dissolution and Oral Absorption of Lipophilic Drugs," International Journal of Pharmaceutics 106(1):15-23, May 1994.

Soliman, M.S., and M.A. Khan, "Preparation and In Vitro Characterization of a Semi-Solid Dispersion of Flurbiprofen With Gelucire 44/14 and Labrasol," Die Pharmazie—An International Journal of Pharmaceutical Sciences 60(4):288-293, Apr. 2005.

International Search Report mailed Feb. 10, 2011, issued in corresponding International Application No. PCT/CA2010/001687, filed Oct. 26, 2010, 11 pages.

* cited by examiner

STABILIZED FORMULATION FOR ORAL ADMINISTRATION OF THERAPEUTIC AGENTS AND RELATED METHODS

CROSS-REFERENCES TO RELATED APPLICATIONS

This application is a continuation of PCT/CA2010/001687, filed Oct. 26, 2010, which claims the benefit U.S. Provisional Application No. 61/365,708, filed Jul. 19, 2010, and U.S. Provisional Application No. 61/255,008, filed Oct. 26, 2009. Each application is incorporated herein by reference in its entirety.

BACKGROUND OF THE INVENTION

Each year in the Indian subcontinent alone, over 500,000 individuals play host to *Leishmania donovani*, an insidious parasite that invades macrophages, rapidly infiltrates the vital organs and ultimately leads to severe infection of the visceral reticuloendothelial system. Visceral leishmaniasis, also known as Kala-azar, is most prevalent in the weak and the young within a population. Left untreated, almost all infected individuals will die. Visceral leishmaniasis affects over 200 million people from 62 countries. The therapeutic arsenal against *Leishmania* is limited to a small number of parenterally administered agents, with daily injections of pentavalent antimony compound. Although more expensive than the antimonials, amphotericin B (AmpB) has a 97% cure rate and no reported resistance. However, drug therapy involves IV administration over 30-40 days and is associated with infusion-related side-effects (fever, chills, bone pain, thrombophlebitis). The dose-limiting toxicity, which may even affect the ability to achieve a cure, is renal impairment. In addition, due to the prohibitive cost and difficult route of drug administration, amphotericin B is failing to reach many patients.

In developed nations, disseminated fungal infections such as candidiasis, histoplasmosis, coccidiosis, and aspergillosis are on the rise, affecting patients with cancer, organ transplant recipients, diabetics and those with HIV/AIDS. In these patients, invasive fungal infections may account for as many as 30% of deaths. Despite the development of a number of new antifungal agents, amphotericin B formulated as an IV administered micelle and liposomal dispersion remains one of the most effective agents in the treatment of systemic fungal infections. In addition, a variety of parenteral formulation approaches have been studied for AmpB. While effective, the limitations of these parenteral formulations of amphotericin B are the safety issues associated with administration (infection of the indwelling catheter, patient chills and shaking due to RBC haemolysis, dose-dependent renal toxicity), feasibility of administration of parenteral products in remote locations and high drug cost.

The development of an effective, stable, and safe oral formulation of amphotericin B that would have significant applications in the treatment of disseminated fungal infections and would dramatically expand access to treatment of visceral leishmaniasis. However, the bioavailability of AmpB is negligible due to low aqueous solubility and instability at the low pH found in gastric fluid. Such limitations also apply to a variety of other therapeutic agents for which oral formulations are desirable.

A need exists for effective, stable, and safe oral formulations of amphotericin B as well as many other therapeutic agents that provide for enhanced bioavailability and/or increased stability of the therapeutic agent of interest the low pH found in gastric fluid. The present invention seeks to fulfill these needs and provides further related advantages.

SUMMARY OF THE INVENTION

The present invention provides thermally stable compositions for formulating therapeutic agents, thermally stable therapeutic agent formulations based on the compositions, methods for administering therapeutic agents using the formulations, and methods for treating conditions and diseases using the formulations.

In one aspect, the invention provides an amphotericin B formulation, comprising,
(a) amphotericin B;
(b) one or more fatty acid glycerol esters;
(c) one or more polyethylene oxide-containing fatty acid esters; and
(d) a tocopherol polyethylene glycol succinate.

In one embodiment, amphotericin B is present in the formulation in an amount from about 0.5 to about 10 mg/mL of the formulation. In one embodiment, amphotericin B is present in the formulation in about 5 mg/mL. In another embodiment, amphotericin B is present in the formulation in about 7 mg/mL.

In one embodiment, the fatty acid glycerol esters comprise from about 32 to about 52% by weight fatty acid monoglycerides. In one embodiment, the fatty acid glycerol esters comprise from about 30 to about 50% by weight fatty acid diglycerides. In one embodiment, the fatty acid glycerol esters comprise from about 5 to about 20% by weight fatty acid triglycerides. In one embodiment, the fatty acid glycerol esters comprise greater than about 60% by weight oleic acid mono-, di-, and triglycerides.

In one embodiment, the polyethylene oxide-containing fatty acid esters comprise a polyethylene oxide ester of a C8-C22 saturated fatty acid. In one embodiment, the polyethylene oxide-containing fatty acid esters comprise a polyethylene oxide ester of a C12-C18 saturated fatty acid. In one embodiment, the polyethylene oxide-containing fatty acid esters are selected from the group consisting of lauric acid esters, palmitic acid esters, stearic acid esters, and mixtures thereof. In one embodiment, the polyethylene oxide-containing fatty acid esters comprise a polyethylene oxide having an average molecular weight of from about 750 to about 2000.

In one embodiment, the ratio of the fatty acid glycerol esters to polyethylene oxide-containing fatty acid esters is from about 20:80 to about 80:20 v/v. In one embodiment, the ratio of the fatty acid glycerol esters to polyethylene oxide-containing fatty acid esters is about 60:40 v/v.

In one embodiment, the tocopherol polyethylene glycol succinate is present in the formulation from about 0.1 to about 10 percent by volume based on the total volume of the formulation. In one embodiment, the tocopherol polyethylene glycol succinate is present in the formulation in about 5 percent by volume based on the total volume of the formulation.

In one embodiment, the formulation further comprises glycerol in an amount less than about 10% by weight.

In one embodiment, the formulation is a self-emulsifying drug delivery system.

In another aspect, the invention provides a method for administering amphotericin B, comprising administering an amphotericin B formulation of the invention to a subject in need thereof. In one embodiment, the formulation is administered orally.

In another aspect, the invention provides a method for treating an infectious disease treatable by the administration of amphotericin B, comprising administering to a subject in need thereof a therapeutically effective amount of an amphotericin B formulation of the invention. In one embodiment, the formulation is administered orally. In another embodiment, the formulation is administered topically.

Diseases treatable by the formulations include fungal infections, visceral leishmaniasis, cutaneous leishmaniasis, Chagas disease, Alzheimer's disease, or Febrile neutropenia. Fungal infections treatable by the formulations include aspergillosis, blastomycosis, candidiasis, coccidioidomycosis, crytococcosis, histoplasmosis, mucormycosis, paracoccidioidomycosis, or sporotrichosis.

In another aspect, the invention provides a formulation for the delivery of a therapeutic agent, comprising,
 (a) a therapeutic agent;
 (b) one or more fatty acid glycerol esters;
 (c) one or more polyethylene oxide-containing fatty acid esters; and
 (d) a tocopherol polyethylene glycol succinate.

In one embodiment, the therapeutic agent is present in the formulation in an amount from about 0.1 mg/mL to about 25 mg/mL of the formulation.

In certain embodiments, the therapeutic agent is selected from the group consisting of anticancers, antibiotics, antiviral drugs, antimycotics, anti-prions, anti-amoebics, non-steroidal anti-inflammatory drugs, anti-allergics, immunosuppressive agents, coronary drugs, analgesics, local anesthetics, anxiolytics, sedatives, hypnotics, migraine relieving agents, drugs against motion sickness, and anti-emetics.

In certain embodiments, the therapeutic agent is selected from the group consisting of tetracycline, doxycycline, oxytetracycline, chloramphenicol, erythromycin, acyclovir, idoxuridine, tromantadine, miconazole, ketoconazole, fluconazole, itraconazole, econazole, griseofulvin, amphotericin B, nystatine, metronidazole, metronidazole benzoate, tinidazole, indomethacin, ibuprofen, piroxicam, diclofenac, disodium cromoglycate, nitroglycerin, isosorbide dinitrate, verapamile, nifedipine, diltiazem, digoxine, morphine, cyclosporins, buprenorphine, lidocaine, diazepam, nitrazepam, flurazepam, estazolam, flunitrazepam, triazolam, alprazolam, midazolam, temazepam lormetazepam, brotizolam, clobazam, clonazepam, lorazepam, oxazepam, busiprone, sumatriptan, ergotamine derivatives, cinnarizine, anti-histamines, ondansetron, tropisetron, granisetrone, metoclopramide, disulfuram, vitamin K, paclitaxel, docetaxel, camptothecin, SN38, cisplatin, and carboplatin.

In one embodiment, the formulation further comprises a second therapeutic agent.

In one embodiment, the fatty acid glycerol esters comprise from about 32 to about 52% by weight fatty acid monoglycerides. In one embodiment, the fatty acid glycerol esters comprise from about 30 to about 50% by weight fatty acid diglycerides. In one embodiment, the fatty acid glycerol esters comprise from about 5 to about 20% by weight fatty acid triglycerides. In one embodiment, the fatty acid glycerol esters comprise greater than about 60% by weight oleic acid mono-, di-, and triglycerides.

In one embodiment, the polyethylene oxide-containing fatty acid esters comprise a polyethylene oxide ester of a C8-C22 saturated fatty acid. In one embodiment, the polyethylene oxide-containing fatty acid esters comprise a polyethylene oxide ester of a C12-C18 saturated fatty acid. In one embodiment, the polyethylene oxide-containing fatty acid esters are selected from the group consisting of lauric acid esters, palmitic acid esters, stearic acid esters, and mixtures thereof. In one embodiment, the polyethylene oxide-containing fatty acid esters comprise a polyethylene oxide having an average molecular weight of from about 750 to about 2000.

In one embodiment, the ratio of the fatty acid glycerol esters to polyethylene oxide-containing fatty acid esters is from about 20:80 to about 80:20 v/v. In one embodiment, the ratio of the fatty acid glycerol esters to polyethylene oxide-containing fatty acid esters is about 60:40 v/v. In another embodiment, the ratio of the fatty acid glycerol esters to polyethylene oxide-containing fatty acid esters is about 60:40 v/v.

In one embodiment, the tocopherol polyethylene glycol succinate is present in the formulation from about 0.1 to about 10 percent by volume based on the total volume of the formulation. In one embodiment, the tocopherol polyethylene glycol succinate is present in the formulation in about 5 percent by volume based on the total volume of the formulation.

In one embodiment, the formulation further comprises glycerol in an amount less than about 10% by weight.

In one embodiment, the formulation is a self-emulsifying drug delivery system.

In another aspect, the invention provides a method for administering a therapeutic agent, comprising administering a therapeutic agent formulation of the invention to a subject in need of such agent. In one embodiment, the formulation is administered orally. In another embodiment, the formulation is administered topically.

In another aspect, the invention provides a composition for formulating a therapeutic agent, comprising,
 (a) one or more fatty acid glycerol esters;
 (b) one or more polyethylene oxide-containing fatty acid esters; and
 (c) a tocopherol polyethylene glycol succinate.

In one embodiment, the fatty acid glycerol esters comprise from about 32 to about 52% by weight fatty acid monoglycerides. In one embodiment, the fatty acid glycerol esters comprise from about 30 to about 50% by weight fatty acid diglycerides. In one embodiment, the fatty acid glycerol esters comprise from about 5 to about 20% by weight fatty acid triglycerides. In one embodiment, the fatty acid glycerol esters comprise greater than about 60% by weight oleic acid mono-, di-, and triglycerides.

In one embodiment, the polyethylene oxide-containing fatty acid esters comprise a polyethylene oxide ester of a C8-C22 saturated fatty acid. In one embodiment, the polyethylene oxide-containing fatty acid esters comprise a polyethylene oxide ester of a C12-C18 saturated fatty acid. In one embodiment, the polyethylene oxide-containing fatty acid esters is selected from the group consisting of lauric acid esters, palmitic acid esters, stearic acid esters, and mixtures thereof. In one embodiment, the polyethylene oxide-containing fatty acid esters comprise a polyethylene oxide having an average molecular weight of from about 750 to about 2000.

In one embodiment, the tocopherol polyethylene glycol succinate is present in the formulation from about 0.1 to about 10 percent by volume based on the total volume of the formulation. In one embodiment, the tocopherol polyethylene glycol succinate is present in the formulation in about 5 percent by volume based on the total volume of the formulation.

In one embodiment, the composition further comprises glycerol in an amount less than about 10% by weight.

In another aspect, the invention provides a method for formulating a therapeutic agent, comprising combining a therapeutic agent with a composition of the invention for formulating a therapeutic agent.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1:
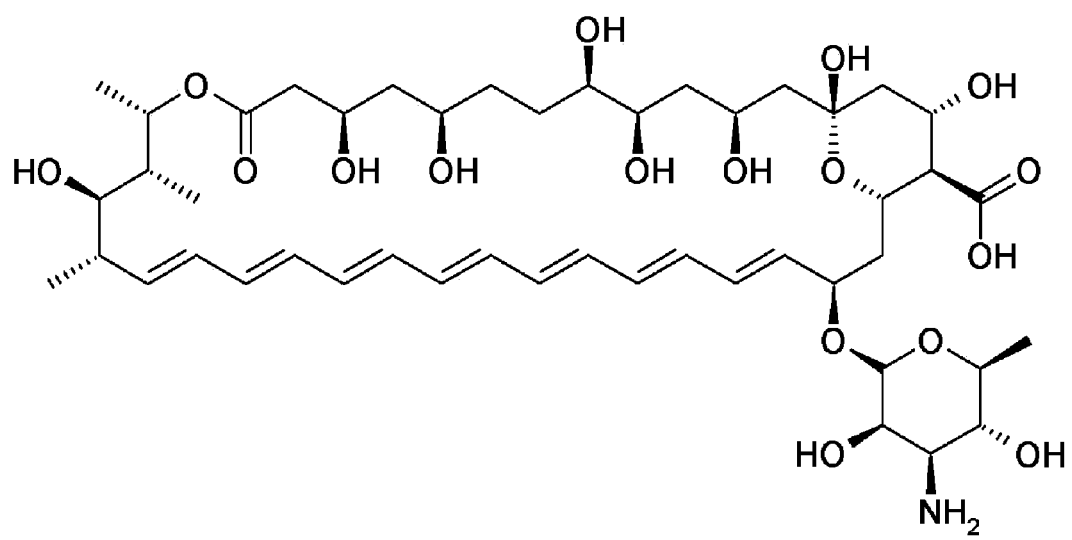
FIG. 1 illustrates the chemical structure of amphotericin B (AmpB).

The present invention provides stable compositions for formulating therapeutic agents. The compositions are effective for solubilizing therapeutic agents, particularly difficultly soluble therapeutic agents. The compositions advantageously enhance the bioavailability of the therapeutic agents and have prolonged thermal stability. The invention also provides therapeutic agent formulations based on the compositions that are effective for the delivery of therapeutic agents, particularly oral administration of therapeutic agents. Amphotericin B formulations are used herein as the prototypic example, however, one of skill in the art will appreciate that such formulations are applicable to a variety of therapeutic agents. Accordingly, in one aspect, the invention provides amphotericin B formulations based on the compositions. The amphotericin B formulations effectively solubilize amphotericin B providing formulations having increased amphotericin B concentrations and, at the same time, provide for enhanced amphotericin B bioavailability.

Amphotericin B Formulations

In one aspect, the present invention provides amphotericin B formulations, methods for making the formulations, methods for administering amphotericin B using the formulations, and methods for treating diseases treatable by amphotericin B by administering the formulations.

Amphotericin B is an effective antifungal agent, and at present, is the drug of choice for treating most serious systemic fungal infections. The drug binds strongly to ergosterol, a major sterol component of fungal membranes, forming pores in the membranes causing disruption of the membrane, cell permeability, and lysis.

Amphotericin B has had limitations in clinical administration due to several unfavorable properties. First, amphotericin B has a strong binding affinity for cholesterol, a sterol present in most mammalian cell membranes, and therefore is capable of disrupting host cells. This leads to renal toxicity of the drug. Second, amphotericin B is not absorbed in the gastrointestinal tract (GIT) due to its poor solubility and its sensitivity to the acid environment of the stomach. To overcome this problem, amphotericin B is used parenterally as liposomal (AMPBISOME®) or as colloidal dispersion (FUNGIZONE®, ABELCET®) for the treatment of certain systemic fungal infections (Arikan and Rex, 2001. Lipid-based antifungal agents: current status. *Curr. Pharm. Des.* 5:393-415).

However, intravenous injection and infusion of amphotericin B have significant disadvantages. First, the intravenous injection and infusion of amphotericin B has been associated with considerable fluctuation of drug concentrations in the blood and side effects such as nephrotoxicity (Müller et al., 2000, Nanosuspensions for the formulation of poorly soluble drugs-rationale for development and what we can expect for the future. In: Nielloud, F., Marti-Mestres, G. (Eds.), Pharmaceutical emulsions and suspensions. Plenum Press/Marcel Dekker, New York, pp. 383-408). Second, in addition to the high cost, the injection and infusion formulation of amphotericin B have also presented low compliance and technical problems with administration in endemic countries.

In one embodiment, the present invention overcomes these disadvantages by providing an amphotericin B formulation that can be administered orally. The oral amphotericin B formulations of the invention can be expected to improve patient compliance and to improve pharmacokinetics of the drug and to increase the amphotericin B absorption in GI tract.

Amphotericin B is an antimycotic polyene antibiotic obtained from *Streptomyces nodosus* M4575. Amphotericin B is designated chemically as [1R-(1R*,3S*,5R*,6R*,9R*, 11R*,15S*,16R*,17R*,18S*,19E,21E,23E,25E, 27E,29E, 31E,33R*,35S*,36R*,37S,)]-33-[(3-amino-3,6-dideoxy-β-D-mannopyranosyl)oxy]1,3,5,6,9,11,17,37-octahydroxy-15,16,18-trimethyl-13-oxo-14,39-dioxabicyclo-[33.3.1] nonatriaconta-19,21,23,25,27,29,31-heptaene-36-carboxylic acid. The chemical structure of amphotericin B is shown in FIG. 1. Crystalline amphotericin B is insoluble in water.

In one aspect, the present invention provides amphotericin B formulations. The amphotericin formulations of the invention include
 (a) amphotericin B;
 (b) one or more fatty acid glycerol esters;
 (c) one or more polyethylene oxide-containing fatty acid esters; and
 (d) optionally a tocopherol polyethylene glycol succinate.

In representative formulations, amphotericin B is present in an amount from about 0.5 to about 10 mg/mL of the formulation. In one embodiment, amphotericin B or pharmaceutically acceptable salt thereof is present in the formulation in about 5 mg/mL. In one embodiment, amphotericin B or its pharmaceutically acceptable salt thereof is present in the formulation in about 7 mg/mL. In one embodiment, the formulation includes a tocopherol polyethylene glycol succinate.

Fatty Acid Glycerol Esters.

The amphotericin B formulations include one or more fatty acid glycerol esters, and typically, a mixture of fatty acid glycerol esters. As used herein the term "fatty acid glycerol esters" refers to esters formed between glycerol and one or more fatty acids including mono-, di-, and tri-esters (i.e., glycerides). Suitable fatty acids include saturated and unsaturated fatty acids having from eight (8) to twenty-two (22) carbons atoms (i.e., C8-C22 fatty acids). In certain embodiments, suitable fatty acids include C12-C18 fatty acids.

The fatty acid glycerol esters useful in the formulations can be provided by commercially available sources. A representative source for the fatty acid glycerol esters is a mixture of mono-, di-, and triesters commercially available as PECEOL® (Gattéfossé, Saint Priest Cedex, France), commonly referred to as "glyceryl oleate" or "glyceryl monooleate." When PECEOL® is used as the source of fatty acid glycerol esters in the formulations, the fatty acid glycerol esters comprise from about 32 to about 52% by weight fatty acid monoglycerides, from about 30 to about 50% by weight fatty acid diglycerides, and from about 5 to about 20% by weight fatty acid triglycerides. The fatty acid glycerol esters comprise greater than about 60% by weight oleic acid (C18: 1) mono-, di-, and triglycerides. Other fatty acid glycerol esters include esters of palmitic acid (C16) (less than about 12%), stearic acid (C18) (less than about 6%), linoleic acid (C18:2) (less than about 35%), linolenic aid (C18:3) (less than about 2%), arachidic acid (C20) (less than about 2%), and eicosenoic acid (C20:1) (less than about 2%). PECEOL® can also include free glycerol (typically about 1%). In one embodiment, the fatty acid glycerol esters comprise about 44% by weight fatty acid monoglycerides, about 45% by weight fatty acid diglycerides, and about 9% by weight fatty acid triglycerides, and the fatty acid glycerol esters comprise about 78% by weight oleic acid (C18:1) mono-, di-, and triglycerides. Other fatty acid glycerol esters include esters of palmitic acid (C16) (about 4%), stearic acid (C18) (about 2%), linoleic acid (C18:2) (about 12%), linolenic aid (C18:3) (less than 1%), arachidic acid (C20) (less than 1%), and eicosenoic acid (C20:1) (less than 1%).

In certain embodiments, the formulations of the invention can include glycerol in an amount less than about 10% by weight.

Polyethylene Oxide-Containing Fatty Acid Esters.

As noted above, the amphotericin B formulations include one or more polyethoxylated lipids such as one or more polyethylene oxide-containing fatty acid esters, and typically, a mixture of polyethylene oxide-containing fatty acid esters.

Accordingly, in one embodiment, the amphotericin B formulations of the invention include
 (a) amphotericin B;
 (b) one or more fatty acid glycerol esters;
 (c) one or more polyethylene oxide-containing fatty acid esters; and
 (d) optionally a tocopherol polyethylene glycol succinate.

As used herein, the term "polyethylene oxide-containing fatty acid ester" refers to a fatty acid ester that includes a polyethylene oxide group (i.e., polyethylene glycol group) covalently coupled to the fatty acid through an ester bond. Polyethylene oxide-containing fatty acid esters include mono- and di-fatty acid esters of polyethylene glycol. Suitable polyethylene oxide-containing fatty acid esters are derived from fatty acids including saturated and unsaturated fatty acids having from eight (8) to twenty-two (22) carbons atoms (i.e., a polyethylene oxide ester of a C8-C22 fatty acid). In certain embodiments, suitable polyethylene oxide-containing fatty acid esters are derived from fatty acids including saturated and unsaturated fatty acids having from twelve (12) to eighteen (18) carbons atoms (i.e., a polyethylene oxide ester of a C12-C18 fatty acid). Representative polyethylene oxide-containing fatty acid esters include saturated C8-C22 fatty acid esters. In certain embodiments, suitable polyethylene oxide-containing fatty acid esters include saturated C12-C18 fatty acids.

The molecular weight of the polyethylene oxide group of the polyethylene oxide-containing fatty acid ester can be varied to optimize the solubility of the therapeutic agent (e.g., amphotericin B) in the formulation. Representative average molecular weights for the polyethylene oxide groups can be from about 350 to about 2000. In one embodiment, the average molecular weight for the polyethylene oxide group is about 1500.

In this embodiment, the amphotericin B formulations include one or more polyethylene oxide-containing fatty acid esters, and typically, a mixture of polyethylene oxide-containing fatty acid esters (mono- and di-fatty acid esters of polyethylene glycol).

The polyethylene oxide-containing fatty acid esters useful in the formulations can be provided by commercially available sources. Representative polyethylene oxide-containing fatty acid esters (mixtures of mono- and diesters) are commercially available under the designation GELUCIRE® (Gattéfossé, Saint Priest Cedex, France). Suitable polyethylene oxide-containing fatty acid esters can be provided by GELUCIRE® 44/14, GELUCIRE® 50/13, and GELUCIRE® 53/10. The numerals in these designations refer to the melting point and hydrophilic/lipophilic balance (HLB) of these materials, respectively. GELUCIRE® 44/14, GELUCIRE® 50/13, and GELUCIRE® 53/10 are mixtures of (a) mono-, di-, and triesters of glycerol (glycerides) and (b) mono- and diesters of polyethylene glycol (macrogols). The GELUCIRES can also include free polyethylene glycol (e.g., PEG 1500).

Lauric acid (C12) is the predominant fatty acid component of the glycerides and polyethylene glycol esters in GELUCIRE® 44/14. GELUCIRE® 44/14 is referred to as a mixture of glyceryl dilaurate (lauric acid diester with glycerol) and PEG dilaurate (lauric acid diester with polyethylene glycol), and is commonly known as PEG-32 glyceryl laurate (Gattéfossé) lauroyl macrogol-32 glycerides EP, or lauroyl polyoxylglycerides USP/NF. GELUCIRE® 44/14 is produced by the reaction of hydrogenated palm kernel oil with polyethylene glycol (average molecular weight 1500). GELUCIRE® 44/14 includes about 20% mono-, di- and, triglycerides, about 72% mono- and di-fatty acid esters of polyethylene glycol 1500, and about 8% polyethylene glycol 1500.

GELUCIRE® 44/14 includes lauric acid (C12) esters (30 to 50%), myristic acid (C14) esters (5 to 25%), palmitic acid (C16) esters (4 to 25%), stearic acid (C18) esters (5 to 35%), caprylic acid (C8) esters (less than 15%), and capric acid (C10) esters (less than 12%). GELUCIRE® 44/14 may also include free glycerol (typically less than about 1%). In a representative formulation, GELUCIRE® 44/14 includes lauric acid (C12) esters (about 47%), myristic acid (C14) esters (about 18%), palmitic acid (C16) esters (about 10%), stearic acid (C18) esters (about 11%), caprylic acid (C8) esters (about 8%), and capric acid (C10) esters (about 12%).

Palmitic acid (C16) (40-50%) and stearic acid (C18) (48-58%) are the predominant fatty acid components of the glycerides and polyethylene glycol esters in GELUCIRE® 50/13. GELUCIRE® 50/13 is known as PEG-32 glyceryl palmitostearate (Gattéfossé), stearoyl macrogolglycerides EP, or stearoyl polyoxylglycerides USP/NF). GELUCIRE® 50/13 includes palmitic acid (C16) esters (40 to 50%), stearic acid (C18) esters (48 to 58%) (stearic and palmitic acid esters greater than about 90%), lauric acid (C12) esters (less than 5%), myristic acid (C14) esters (less than 5%), caprylic acid (C8) esters (less than 3%), and capric acid (C10) esters (less than 3%). GELUCIRE® 50/13 may also include free glycerol (typically less than about 1%). In a representative formulation, GELUCIRE® 50/13 includes palmitic acid (C16) esters (about 43%), stearic acid (C18) esters (about 54%) (stearic and palmitic acid esters about 97%), lauric acid (C12) esters (less than 1%), myristic acid (C14) esters (about 1%), caprylic acid (C8) esters (less than 1%), and capric acid (C10) esters (less than 1%)

Stearic acid (C18) is the predominant fatty acid component of the glycerides and polyethylene glycol esters in GELUCIRE® 53/10. GELUCIRE® 53/10 is known as PEG-32 glyceryl stearate (Gattéfossé).

In one embodiment, the polyethylene oxide-containing fatty acid ester is a lauric acid ester, a palmitic acid ester, or a stearic acid ester (i.e., mono- and di-lauric acid esters of polyethylene glycol, mono- and di-palmitic acid esters of polyethylene glycol, mono- and di-stearic acid esters of polyethylene glycol). Mixtures of these esters can also be used.

For embodiments that include polyethylene oxide-containing fatty acid esters, the ratio of the fatty acid glycerol esters to polyethylene oxide-containing fatty acid esters is from about 20:80 to about 80:20 v/v. In one embodiment, the ratio of the fatty acid glycerol esters to polyethylene oxide-containing fatty acid esters is about 30:70 v/v. In one embodiment, the ratio of the fatty acid glycerol esters to polyethylene oxide-containing fatty acid esters is about 40:60 v/v. In one embodiment, the ratio of the fatty acid glycerol esters to polyethylene oxide-containing fatty acid esters is about 50:50 v/v. In one embodiment, the ratio of the fatty acid glycerol esters to polyethylene oxide-containing fatty acid esters is about 60:40 v/v. In one embodiment, the ratio of the fatty acid glycerol esters to polyethylene oxide-containing fatty acid esters is about 70:30 v/v.

In one embodiment, the amphotericin B formulations of the invention include
(a) amphotericin B;
(b) oleic acid glycerol esters;
(c) lauric acid esters of polyethylene glycol; and
(d) optionally a tocopherol polyethylene glycol succinate.

In another embodiment, the amphotericin B formulations of the invention include
(a) amphotericin B;
(b) oleic acid glycerol esters;
(c) palmitic and stearic acid esters of polyethylene glycol; and
(d) optionally a tocopherol polyethylene glycol succinate.

In a further embodiment, the amphotericin B formulations of the invention include
(a) amphotericin B;
(b) oleic acid glycerol esters;
(c) stearic acid esters of polyethylene glycol; and
(d) optionally a tocopherol polyethylene glycol succinate.

In one embodiment, the amphotericin B formulation of the invention includes amphotericin B, PECEOL®, and GELUCIRE® 44/14. In another embodiment, the amphotericin B formulation of the invention includes amphotericin B, PECEOL®, and GELUCIRE® 50/13. In a further embodiment, the amphotericin B formulation of the invention includes amphotericin B, PECEOL®, and GELUCIRE® 53/10. In these embodiments, the ratio of PECEOL® to GELUCIRE® can be from 20:80 to 80:20 (e.g., 20:80, 30:70; 40:60; 50:50; 60:40; 70:30; and 80:20).

Tocopherol Polyethylene Glycol Succinate.

As noted above, the amphotericin B formulations optionally include a tocopherol polyethylene glycol succinate (e.g., TPGS or vitamin E TPGS). The tocopherol polyethylene glycol is included in the formulation to enhance the thermal stability of the formulation, which in turn, can increase the formulation's shelf-life, which is particularly important in tropical regions of the world where prolonged exposure to high temperatures are common and refrigerated medicinal storage is rare. For formulations in which enhanced thermal stability is desired, the formulation includes a tocopherol polyethylene glycol succinate.

Structurally, tocopherol polyethylene glycol succinates have a polyethylene glycol (PEG) covalently coupled to tocopherol (e.g., α-tocopherol or vitamin E) through a succinate linker. Because PEG is a polymer, a variety of polymer molecular weights can be used to prepare the TPGS. In one embodiment, the TPGS is tocopherol polyethylene glycol succinate 1000, in which the average molecular weight of the PEG is 1000. One suitable tocopherol polyethylene glycol succinate is vitamin E TPGS commercially available from Eastman.

As used herein, "vitamin E" refers to a family of compounds that includes α-, β-, γ-, and δ-tocopherols and the corresponding tocotrienols.

The preparation of representative amphotericin B formulations of the invention that include fatty acid glycerol esters, polyethylene oxide-containing fatty acid esters, and a tocopherol polyethylene glycol succinate is described in Example 1.

To enhance the thermostability of amphotericin B formulations, a lipid-based vitamin with antioxidant properties (vitamin E TPGS) was added to the AmpB in 50:50 and 60:40 Peceol/Gelucire 44-14 formulations. Temperature stability studies were conducted to determine the stability of the AmpB formulations at elevated temperature. A further consideration in developing AmpB formulations is that the formulation is stable in the high acid environment of the stomach. As high acidity can rapidly degrade many orally delivered drugs, it is important that orally administered AmpB is not degraded in gastric fluid. Consequently, determining the size and composition of the emulsified drops of AmpB in the formulation when incubated in gastric fluid was also evaluated.

Temperature Stability.

The temperature stability of an AmpB/Peceol formulation was compared to two representative AmpB/TPGS formulations of the invention (AmpB/50:50 (v/v) Peceol/Gelucire 44-14+5% v/v vitamin E-TPGS and AmpB/60:40 (v/v) Peceol/Gelucire 44-14/5% v/v vitamin E-TPGS), as described in Example 2.

Figure 2A:
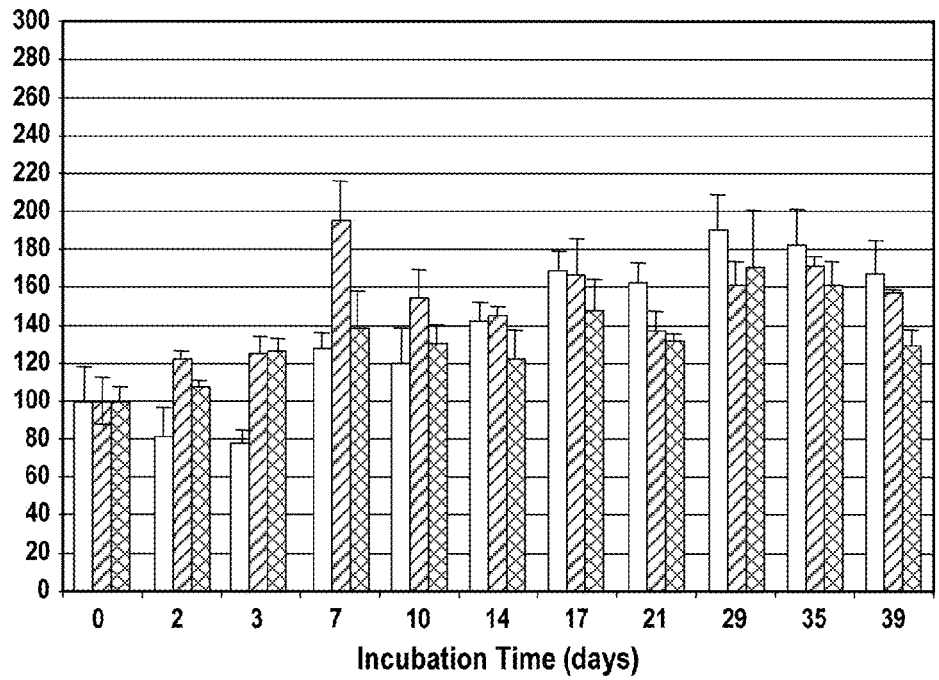
FIG. 2A compares the concentration of AmpB in each of the three AmpB formulations (AmpB/Peceol; and AmpB/Peceol:Gelucire 44-14 (50:50 and 60:40)+5% v/v vitamin E-TPGS) incubated at 4° C. from 0 to 39 days.
Figure 2B:
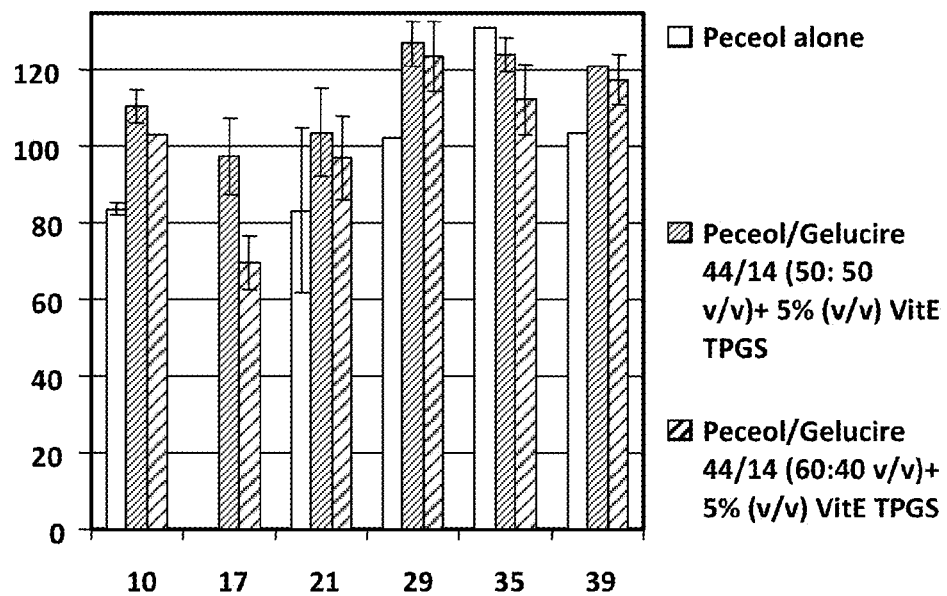
FIG. 2B compares the concentration of AmpB in each of the three AmpB formulations (AmpB/Peceol; and AmpB/Peceol:Gelucire 44-14 (50:50 and 60:40)+5% v/v vitamin E-TPGS) incubated at room temperature over time (10, 17, 21, 29, 35, 39 days).
Figure 2C:
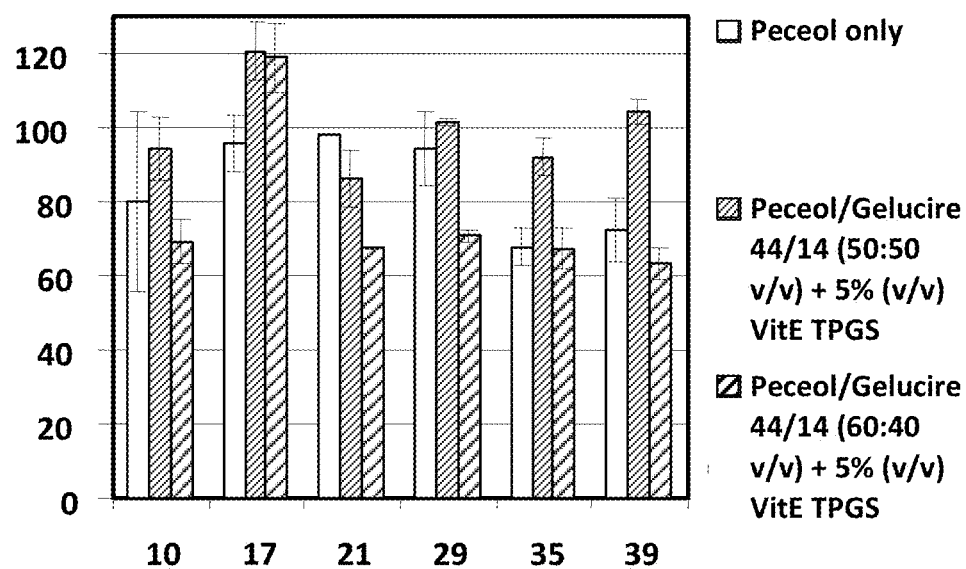
FIG. 2C compares the concentration of AmpB in each of the three AmpB formulations (AmpB/Peceol; and AmpB/Peceol:Gelucire 44-14 (50:50 and 60:40)+5% v/v vitamin E-TPGS) incubated at 43° C. over time (10, 17, 21, 29, 25, 39 days).

The stability of the two TPGS-containing AmpB formulations is compared to the non-TPGS-containing AmpB formulations in FIGS. 2A-2C. FIG. 2A compares the concentration of AmpB in each of the three AmpB formulations incubated at 4° C. over time (0 to 39 days), FIG. 2B compares the concentration of AmpB in each of the three AmpB formulations incubated at RT° C. over time (10, 17, 21, 29, 35, and 39 days), and FIG. 2C compares the concentration of AmpB in each of the three AmpB formulations incubated at 43° C. over time (10, 17, 21, 29, 35, and 39 days).

In the bar graphs of FIGS. 2A-2C, the AmpB concentration in each of three AmpB formulations (percentage of original AmpB concentration) is compared. The first bar in each series represents AmpB concentration for an AmpB/Peceol formulation, the second bar represents AmpB concentration for an AmpB/Peceol:Gelucire 44-14 (50:50)+5% v/v vitamin E-TPGS, and the third bar represents AmpB concentration for an AmpB/Peceol:Gelucire 44-14 (60:40)+5% v/v vitamin E-TPGS.

The concentration of AmpB in the Peceol formulation incubated at room temperature and 43° C. and in Peceol/60:40 Peceol/Gelucire 44-14+5% vitamin E-TPGS exhibited a trend toward a reduction in AmpB concentration over 39 days, whereas AmpB in 50:50 Peceol/Gelucire 44-14+5% vitamin E-TPGS remained relatively stable throughout the study period at both temperatures.

The AmpB concentration remains at greater than 80% of the original concentration after 39 days of incubation at 43° C. for 50:50 Peceol/Gelucire 44-14+5% vitamin E-TPGS and at greater than 60% for AmpB in Peceol alone and in 60:40 Peceol/Gelucire 44-14+5% vitamin E-TPGS. When compared to previous temperature stability studies of AmpB in 60:40 Peceol/Gelucire 44-14 without 5% v/v vitamin E-TPGS (not shown), the formulation with vitamin E-TPGS demonstrates enhanced stability.

Stability in Fasted State Simulated Gastric Fluid (fsSGF).

The stability in fasted state simulated gastric fluid (fsSGF) of two representative AmpB/TPGS formulations of the invention (AmpB/50:50 Peceol/Gelucire 44-14+5% v/v vitamin E-TPGS and AmpB/60:40 Peceol/Gelucire 44-14+5% v/v vitamin E-TPGS) was compared as described in Example 3.

Figure 3:
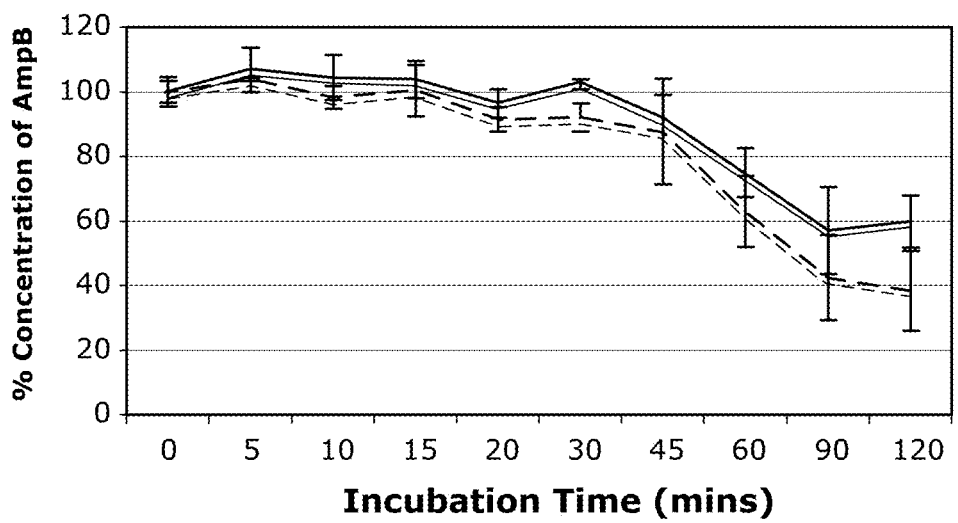
FIG. 3 compares the stability of two representative AmpB/TPGS formulations of the invention (AmpB/Peceol/Gelucire 44-14 (50:50 and 60:40)+5% v/v vitamin E-TPGS) in fasted state simulated gastric fluid (fsSGF) over time. The solid curve represents AmpB concentration in the AmpB/Peceol/Gelucire 44-14 (50:50)+5% v/v vitamin E-TPGS and the dashed curve represents AmpB concentration in the AmpB/Peceol/Gelucire 44-14 (60:40)+5% v/v vitamin E-TPGS.

FIG. 3 compares the stability of two representative AmpB/TPGS formulations of the invention (AmpB/Peceol/Gelucire 44-14 (50:50 and 60:40)+5% v/v vitamin E-TPGS) in fasted state simulated gastric fluid (fsSGF) over time. In FIG. 3, the solid curve represents AmpB concentration in the AmpB/Peceol/Gelucire 44-14 (50:50)+5% v/v vitamin E-TPGS and the dashed curve represents AmpB concentration in the AmpB/Peceol/Gelucire 44-14 (60:40)+5% v/v vitamin E-TPGS.

AmpB in both the 50:50 and 60:40 Peceol/Gelucire 44-14+5% vitamin E-TPGS formulations is stable for at least 45 mins when incubated in fsSGF (FIG. 3). Both formulations indicate approximately equal stability. Although there is a rapid decline of AmpB occurring between 45-90 mins, 50% of AmpB remains after 120 mins. The rate of degradation appears to slow/level off between 90-120 mins.

Emulsion Droplet Size and Distribution.

The emulsion droplet size of two representative AmpB/TPGS formulations of the invention (AmpB/50:50 Peceol/Gelucire 44-14+5% v/v vitamin E-TPGS and AmpB/60:40 Peceol/Gelucire 44-14+5% v/v vitamin E-TPGS) was compared after incubation in fasted state simulated gastric fluid (fsSGF), as described in Example 4.

Emulsified droplet size of AmpB in 50:50 Peceol/Gelucire 44-14/5% v/v vitamin E-TPGS and AmpB in 60:40 Peceol/Gelucire 44-14/5% v/v vitamin E-TPGS after incubation in fsSGF was evaluated concurrently with the stability in fsSGF study. Samples were removed from incubation after 30 mins, 60 mins and 120 mins. Droplet sizes for formulation were determined using a particle-sizer (Malvern Zetasizer 3000 HS). Size distribution was also determined.

Figure 4:
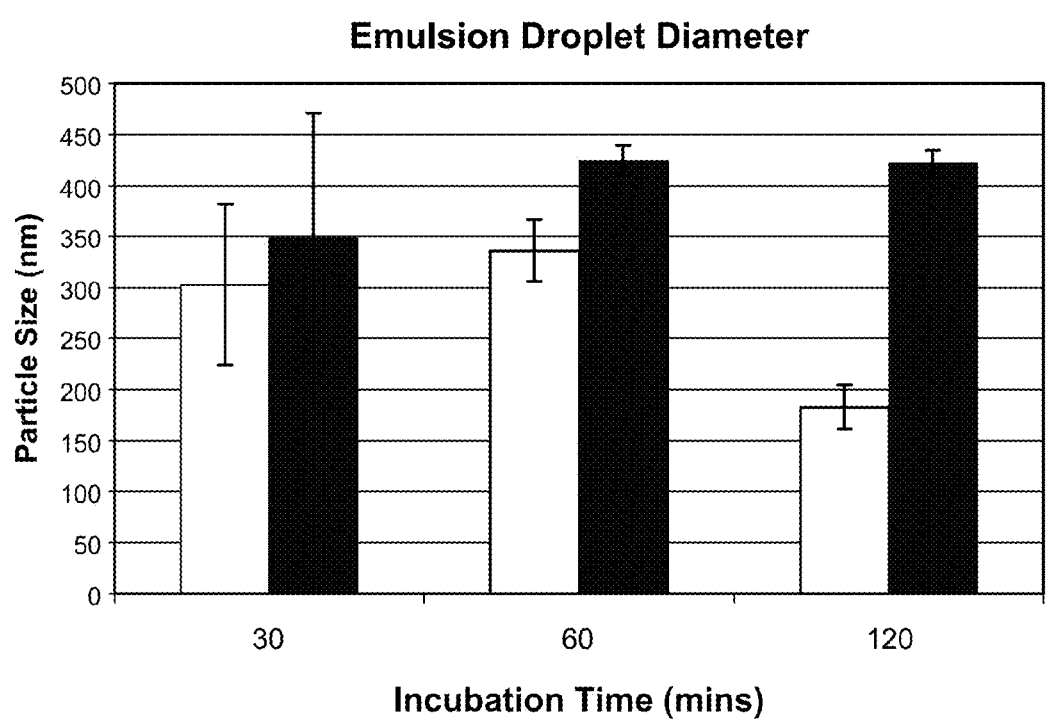
FIG. 4 compares the emulsion droplet size (diameter in nm) of two representative AmpB/TPGS formulations of the invention (AmpB/Peceol/Gelucire 44-14 (50:50 and 60:40)+5% v/v vitamin E-TPGS) after incubation in fasted state simulated gastric fluid (fsSGF). The first bar in each series emulsion droplet diameter for the AmpB/Peceol/Gelucire 44-14 (50:50)+5% v/v vitamin E-TPGS formulation and the second bar represents emulsion droplet size for the AmpB/Peceol/Gelucire 44-14 (60:40)+5% v/v vitamin E-TPGS formulation.

FIG. 4 compares the emulsion droplet size (diameter in nm) of two representative AmpB/TPGS formulations of the invention (AmpB/Peceol/Gelucire 44-14 (50:50 and 60:40)+5% v/v vitamin E-TPGS) after incubation in fasted state simulated gastric fluid (fsSGF). The first bar in each series emulsion droplet diameter for the AmpB/Peceol/Gelucire 44-14 (50:50)+5% v/v vitamin E-TPGS formulation and the second bar represents emulsion droplet size for the AmpB/Peceol/Gelucire 44-14 (60:40)+5% v/v vitamin E-TPGS formulation.

The emulsion droplet size results are presented in FIG. 4. Referring to FIG. 4, the emulsion droplet size of either formulation was consistent over 2 hours incubation in fsSGF. The homogeneity of the sample is indicated by the narrow distribution of mean diameters of the droplets at each time point, as well as the lack of subpopulations. The droplet size distribution indicated that the formulations were substantially homogenous.

Each of the evaluated representative formulations of the invention demonstrated stability in the simulated fluids over the time period evaluated. The stability of the representative amphotericin B formulations in the GI fluids demonstrates their suitability as orally administered formulations.

In one aspect, the invention provides oral formulations of amphotericin B that are stable at the temperatures of WHO Climatic Zones 3 and 4 (30-43° C.). Four representative AmpB formulations were prepared comprising mono- and di-glycerides (Peceol), pegylated esters (Gelucire 44/14), and optionally a vitamin E-TPGS (TPGS). The compositions of the four AmpB formulations are summarized in Table 1.

TABLE 1

Compositions of Representative AmpB Formulations.

| Formulation | AmpB (mg/mL) | Peceol/Gelucire 44/14 (v/v) | TPGS (v/v) |
|---|---|---|---|
| A | 5 | 50:50 | 5 |
| B | 5 | 60:40 | 5 |
| C | 5 | 50:50 | — |
| D | 5 | 60:40 | — |

The stability of the four representative formulations was evaluated and the efficacy of one of the formulations was evaluated in a murine model of visceral leishmaniasis (VL).

Formulation Stability.

Stability testing of four representative oral lipid AmpB formulations composed of mono- and di-glycerides and pegylated esters (Formulation A-Formulation D) was performed over 60 days and analyzed by HPLC-UV. The method for determining the stability of representative AmpB formulations of the invention is described in Example 6.

Figure 5:
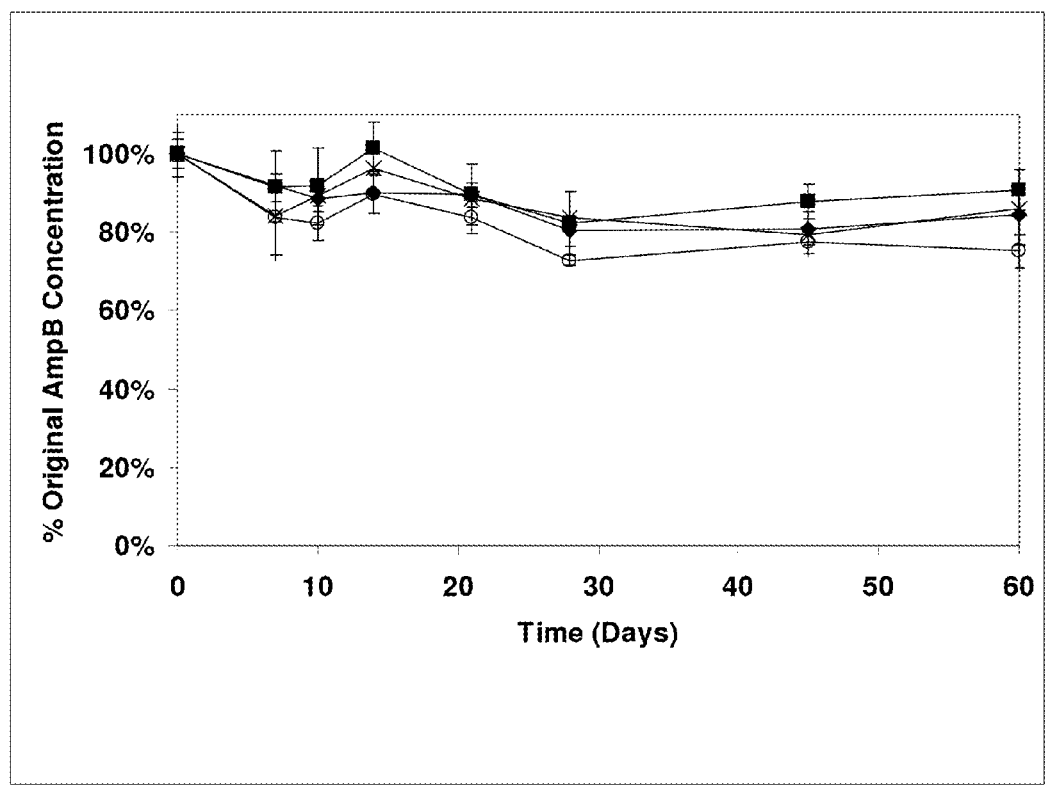
FIG. 5 compares the stability of AmpB in representative lipid formulations of the invention at 30° C. over 60 days (solid diamonds, Formulation A; solid squares, Formulation B; stars, Formulation C; open circles, Formulation D. Data represent mean±SD (n=4)).
Figure 6:
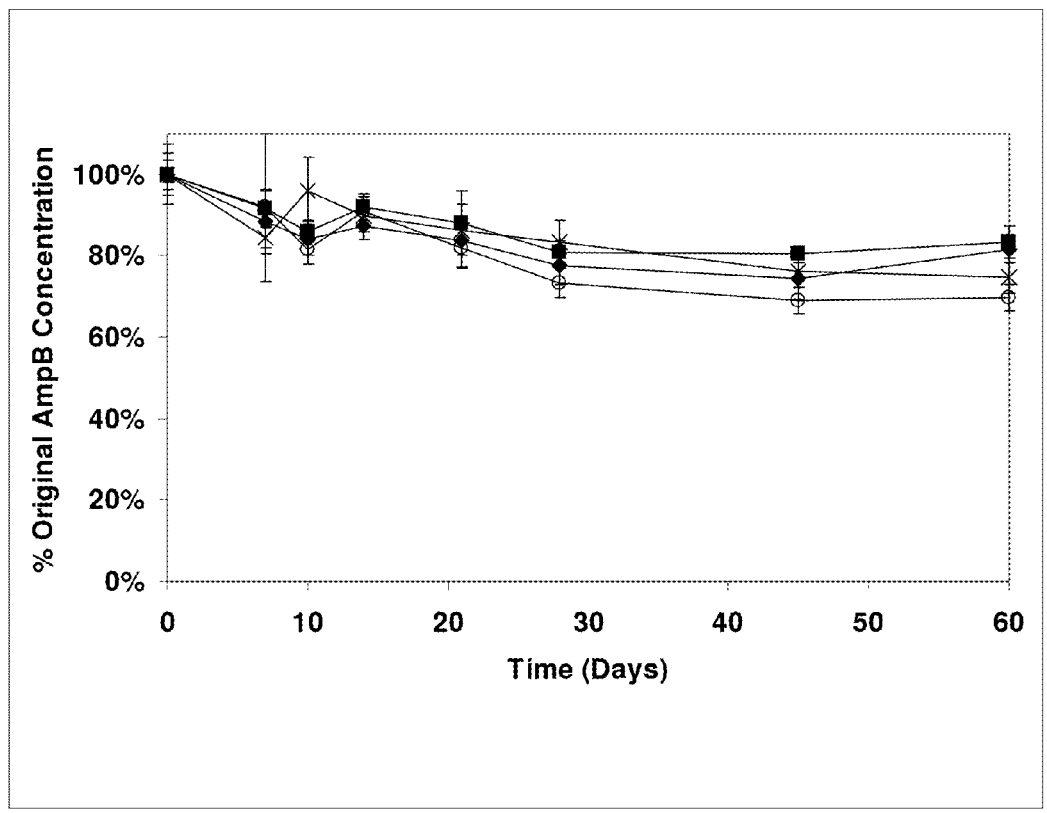
FIG. 6 compares the stability of AmpB in representative lipid formulations of the invention at 43° C. over 60 days (solid diamonds, Formulation A; solid squares, Formulation B; stars, Formulation C; open circles, Formulation D. Data represent mean±SD (n=4)).

FIG. 5 compares the stability of AmpB in representative lipid formulations and demonstrates stability >75% for all formulations over 60 days at 30° C. FIG. 6 shows a similar pattern at 43° C. with a slightly lower concentration in all formulations by 60 days. After 60 days at 30° C., AmpB concentrations were comparable with and without vitamin E-TPGS (about 85% of the original concentration), but when different proportions of mono- and di-glycerides were employed, samples without vitamin E-TPGS (Formulation D) contained only 75% of the original AmpB concentration compared to 91% when vitamin E-TPGS was included (Formulation B). The addition of vitamin E-TPGS did not significantly change the decomposition rate for AmpB in Formulation A at 43° C., although there was a trend to greater retention of AmpB when vitamin E-TPGS was included. The rate of decomposition (μg/mL day) of AmpB in all the lipid formulations at both temperatures is slow, as indicated in Table 2.

TABLE 2

Decomposition rate of AmpB in lipid formulations.

| Formulation | 30° C. μg/mL per day lost | 43° C. μg/mL per day lost |
|---|---|---|
| A | 13.78 ± 4.49 | 16.32 ± 7.25 |
| B | 7.55 ± 5.75 | 13.66 ± 2.07 |
| C | 12.11 ± 9.76 | 21.39 ± 5.08 |
| D | 18.63 ± 5.73 | 25.85 ± 2.34 |

In Table 2, data indicate mean rate of loss of AmpB±SD (n=4). Results derived from the data in FIGS. 5 and 6.

There was a significant decrease (p<0.01) in the rate at which the AmpB was lost in Formulation B compared to Formulation D. This resulted in AmpB concentrations after 60 days at 43° C. that were 83.4% of the original concentration when vitamin E-TPGS was included, but only 69.7% when it was not present.

The temperature stability of AmpB in all the lipid formulations was excellent, exceeding approximately 80% after 60 days at 30° C. (FIG. 5) and 75% at 43° C. (FIG. 6), and exhibiting no clear differences in the pattern of concentration loss versus time among the four preparations. Upon examining the rate of drug loss as a function of excipient composition (Table 2), Formulation B was slightly more stable than Formulation A or Formulation D at 30° C. As expected, addition of vitamin E-TPGS significantly decreased the rate of drug loss at 43° C. At 43° C., the ratio of mono- and di-glycerides and pegylated esters appears less important than the presence of vitamin E-TPGS, as formulations containing it showing a slower rate of AmpB loss.

The stabilities of the formulations of the invention were evaluated up to six months. The formulations demonstrated excellent stability at 30° C. and 43° C.: Formulation A, 85% and 83%; Formulation B, 91% and 84%; Formulation C, 75% and 71%; and Formulation D, 86% and 75% (% AmpB remaining after six months at 30° C. and 43° C., respectively, compared to original concentration).

Stability in Simulated Gastric and Simulated Fasted-State Intestinal Fluid.

Stability of a representative formulation, Formulation A, was evaluated by incubating the formulation for 2 h in simulated gastric fluid (SGF) or for 4 h in fasted-state simulated intestinal fluid (FaSSIF). The methods for determining the stability of representative AmpB formulations of the invention in simulated gastric and simulated fasted-state intestinal fluid are described in Example 7.

Figure 7:
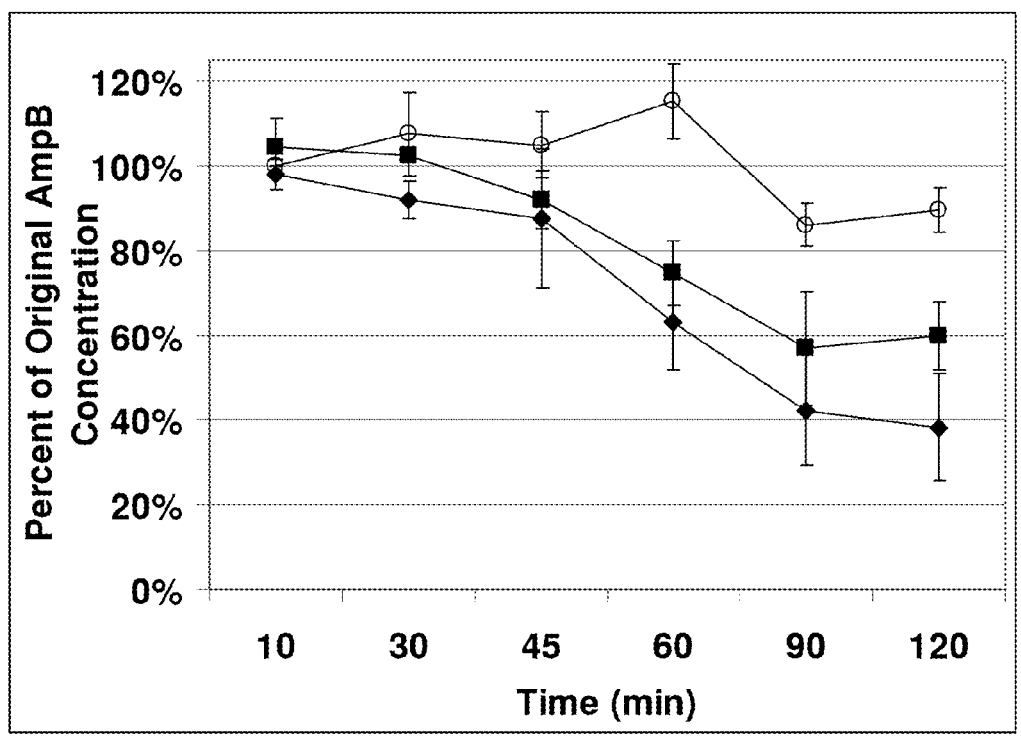
FIG. 7 compares the stability of AmpB in representative lipid formulations of the invention in simulated gastric fluid (SGF) at 37° C. (solid diamonds, Formulation B; solid squares, Formulation A; open circles, Formulation C. Data represent mean±SD (n=3)).

To assess AmpB chemical stability under conditions analogous to the stomach, the AmpB lipid formulations were incubated in simulated gastric fluid (SGF) at 37° C. for 2 h, which is a reasonable time to expect gastric emptying in fasted humans. AmpB in Formulation C retains >90% of its concentration over 1 h in SGF at 37° C. (FIG. 7). When vitamin E-TPGS is included in the lipid formulation, the remaining concentration of AmpB in SGF after 2 h in SGF is 60±8% of the original in the Formulation A formulation and 38±12% for the Formulation B formulation.

Figure 8:
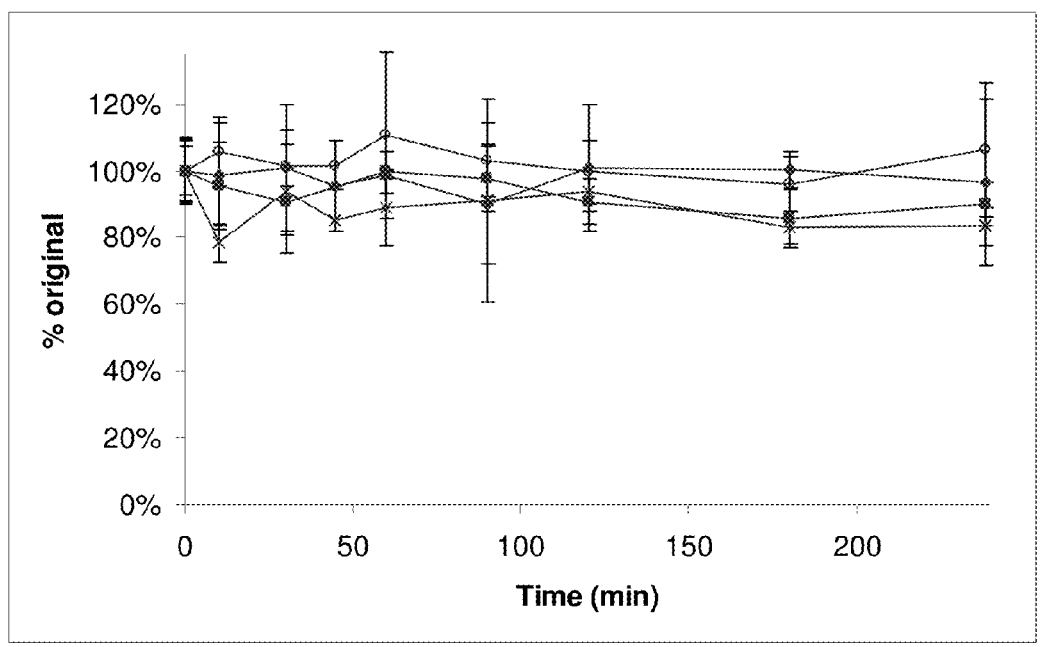
FIG. 8 compares the stability of AmpB in representative lipid formulations of the invention in fasted-state simulated intestinal fluid (FaSSIF) at 37° C. (solid diamonds, Formulation A; solid squares, Formulation B; stars, Formulation C; open circles, Formulation D. Data represent mean±SD (n=3)).

In simulated fasted-state intestinal fluid (FaSSIF), after 4 h of mixing at 37° C., Formulation A retains >95% of its original drug concentration (FIG. 8). Assessment of the stability of AmpB in Formulation B, Formulation C and Formulation D in FaSSIF shows very similar stability of formulations containing vitamin E-TPGS to those without it.

Regarding the properties of these lipid formulations in conditions mimicking those of the gastrointestinal tract, the presence of vitamin E-TPGS decreased AmpB stability in SGF for Formulation A and Formulation B compared to AmpB in Formulation D, declining to <60% by 2 h at 37° C. (FIG. 7). The reduced tolerance of the low pH of 1.2 in SGF could be attributed to increased hydrolysis of AmpB due to an altered emulsion structure in the presence of the hydrophilic surfactant vitamin E-TPGS, perhaps exposing AmpB to the aqueous environment more extensively than when incorporated into mono- and di-glycerides and pegylated esters alone. However, studies of the stability of the lipid formulations in FaSSIF demonstrate that AmpB concentration is well-maintained when incorporated into all of the formulations, as shown in FIG. 8.

Emulsion Droplet Sizing in Simulated Gastric Fluid and Simulated Fasted-State Intestinal Fluid.

The method for determining the emulsion droplet sizing of a representative AmpB formulation of the invention in simulated gastric fluid and simulated fasted-state intestinal fluid stability is described in Example 8.

Figure 9A:
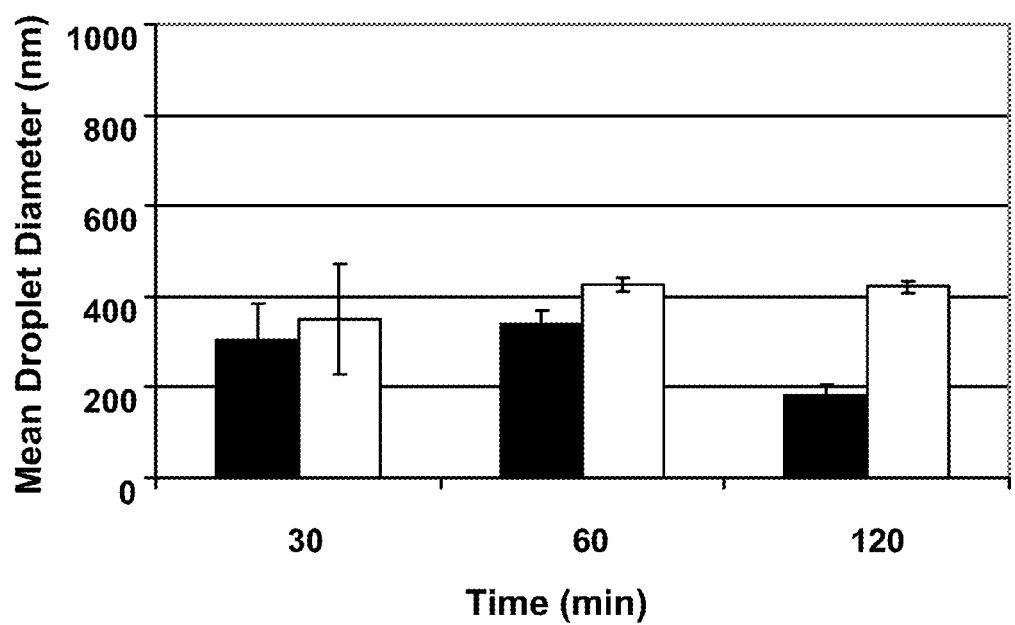
FIG. 9A compares emulsion droplets size of representative lipid formulations of the invention in simulated gastric fluid (gray bars, Formulation A; black bars: Formulation B. Data represent mean±SD (n=3)).
Figure 9B:
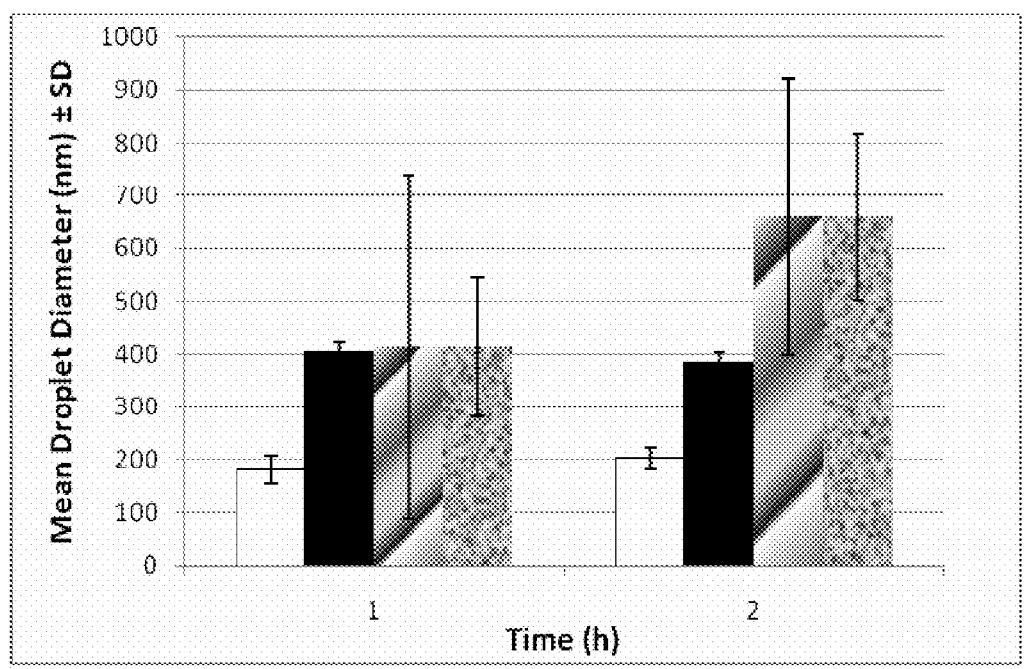
FIG. 9B compares emulsion droplets size of representative lipid formulations of the invention in fasted-state simulated intestinal fluid (white bars, Formulation A; black bars: Formulation B; dotted bars, Formulation C; hatched bars, Formulation D. Data represent mean±SD (n=3)).

Upon mixing AmpB in the lipid formulations in SGF at 37° C. over 2 h, a cloudy emulsion forms spontaneously ("self-emulsifying"). The mean droplet diameter of the emulsion from Formulation A is approximately 300-400 nm, with a decline in mean diameter to <200 nm after 2 h of mixing. For AmpB in Formulation B, the mean droplet diameter is approximately 350-425 nm throughout the 2 h incubation period (FIG. 9A). Assessment of emulsification in FaSSIF of AmpB formulations composed of Peceol/Gelucire 44/14 shows that the presence of vitamin E-TPGS in the Peceol/Gelucire 44/14 mixture, such as in Formulation A and Formulation B, reduces the mean diameter and creates a more monodisperse nanoemulsion. Emulsion droplet sizing of AmpB in Formulation D (no vitamin E-TPGS) following 2 and 4 h mixing in FaSSIF at 37° C. revealed the largest droplet size of approximately 700-850 nm, whereas AmpB in Formulation A (with vitamin E-TPGS) had a relatively smaller mean diameter closer to 200 nm (FIG. 9B).

Considering the similar stability data for the 4 formulations tested (both at elevated temperature and in simulated gastrointestinal fluids) and more desirable self-emulsification properties of Formulation A, this formulation was chosen for in vivo studies of AmpB efficacy in an animal model of VL, as described below.

The self-emulsifying properties of these lipid formulations are deemed important because the formation of a nanoemulsion in the gastrointestinal tract may facilitate intestinal absorption, particularly through the lymphatic transport pathway. Furthermore, a major precipitation of the drug in gastrointestinal fluids would be undesirable and lead to unpredictable absorption patterns. The emulsification of the drug-lipid mixture also promotes interaction with bile salts, which can further enhance solubilization and absorption of the drug in the intestine. The lipid formulations composed of AmpB in mono- and di-glycerides and pegylated esters with vitamin E-TPGS did produce monodisperse nanoemulsions within 30 minutes of mixing with SGF. Formulation A in FaSSIF, which contains sodium taurocholate as the bile salt, produced a slightly larger nanoemulsion of greater polydispersity.

Effectiveness in VL-infected Murine Model.

Visceral leishmaniasis (VL) is a systemic form of a vector-borne parasitic disease caused by obligate intra-macrophage protozoa of the genus *Leishmania*. VL is transmitted via the bite of an infected sand fly. The parasites are then disseminated through the vascular and lymphatic systems, infecting monocytes and macrophages of the reticulo-endothelial system and accumulating in the liver and spleen. VL is always fatal in humans if left untreated.

Anti-leishmanial activity of a representative formulation of the invention (Formulation A) was evaluated at increasing doses (2.5 to 10 mg/kg) in a murine model of VL. The effectiveness of the formulation in the VL-infected murine model is described in Example 9.

Figure 10:
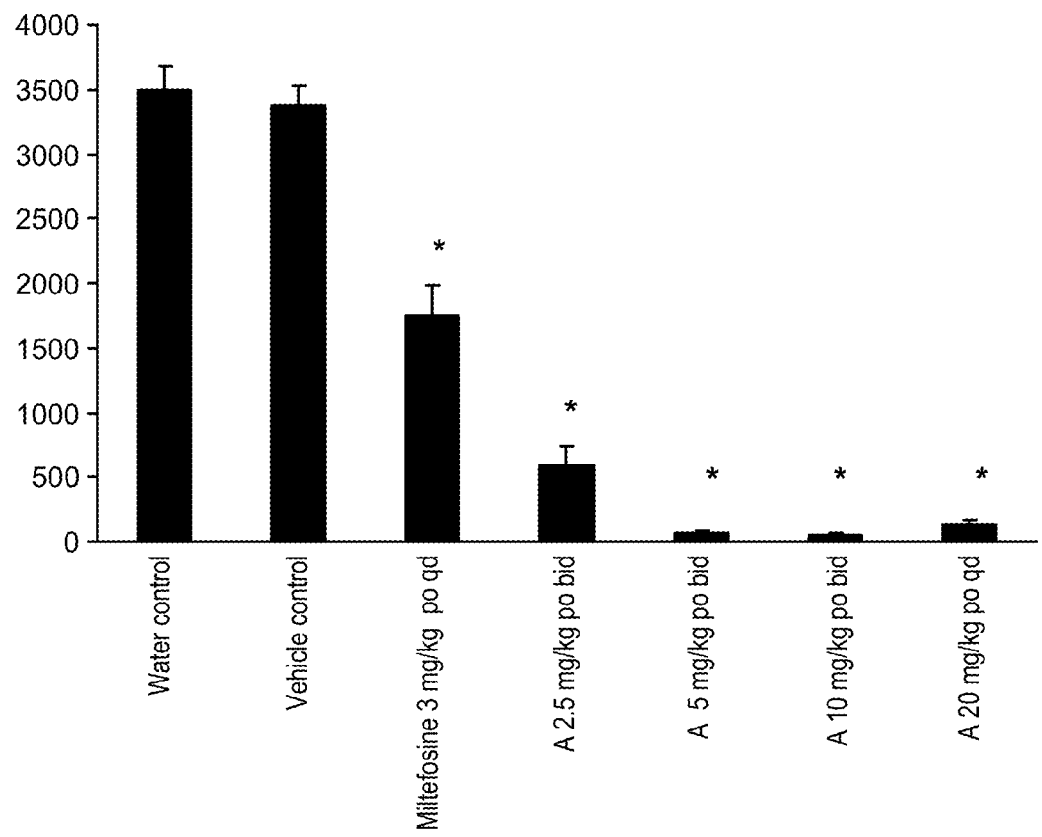
FIG. 10 compares antileishmnial activity of representative lipid formulations of the invention (Formulation A) in *L. donovani*-infected BALB/c mice. Animals were infected and treated as described in Example 9, and LDUs were assessed by microscopic counting of liver smears. All treatments began seven days post infection. Bars of differing letters indicate statistically significant differences within each figure (one-way ANOVA with post-hoc Tukey Multiple Comparisons Test); data are expressed as mean±SD. Groups of animals (n=4) were treated with miltefosine at 3 mg/kg po daily for five days, a lipid-based vehicle control bid po for five days, 2.5, 5 and 10 mg/kg Formulation A bid for five days or 20 mg/kg oral Formulation A po qd for five days. Giemsa stained liver smears were obtained from mice post mortem after no treatment or exposure to vehicle, miltefosine, or the Formulation A at the doses indicated. *: $P<0.05$ compared to vehicle control group. No significant difference between water control and vehicle control groups.

When given in five daily doses at 3 mg/kg po, miltefosine resulted in 47.5±7.0% inhibition of liver parasites. LDU values were not significantly different between groups of animals receiving oral doses of a lipid-based vehicle control bid for five days versus those receiving a single IV saline injection (FIG. 10). Dose response data from treatment of *L. donovani*-infected BALB/c mice with 2.5, 5 and 10 mg/kg Formulation A bid for five days is shown in FIG. 10. Formulation A demonstrated significant efficacy when orally administered to VL-infected mice bid for five days (inhibition of 99%, 98%, and 83% at 10, 5 and 2.5 mg/kg compared to the vehicle control). In addition, the qd dose of 20 mg/kg provided 96% inhibition compared to the vehicle control.

The demonstrated efficacy of the formulation is likely due to a combination of increased solubility, improved gastrointestinal stability and enhanced membrane permeability. In addition, oral administration of a lipid-based formulation favors lymphatic transport. As VL parasites disseminate through the lymphatic and vascular system, infecting macrophages and infiltrating the bone marrow, liver and spleen, the lipid carrier may assist in delivering the drug to the site of greatest infection. These data represent the first tropically stable, oral AmpB formulations to exhibit significant efficacy against *Leishmania donovani* (the parasite responsible for VL) in an infected mouse model.

Self-Emulsifying Drug Delivery Systems

The amphotericin B formulations of the invention can be self-emulsifying drug delivery systems. Self-emulsifying drug delivery systems (SEDDS) are isotropic mixtures of oils, surfactants, solvents, and co-solvents/surfactants. SEDDS can be used for the design of formulations in order to improve the oral absorption of highly lipophilic drug compounds, such as amphotericin B. When a SEDDS composition is released into the lumen of the gut, the composition disperses to form a fine emulsion, so that the drug remains in solution in the gut, avoiding the dissolution step that frequently limits the rate of absorption of hydrophobic drugs from the crystalline state. The use of SEDDS usually leads to improved bioavailability and/or a more consistent temporal profile of absorption from the gut. A description of compositions of SEDDS can be found in C. W. Pouton, *Advanced Drug Delivery Reviews* 25: 47-58 (1997).

The amphotericin B formulations of the invention can be orally administered in soft or hard gelatin capsules and form fine relatively stable oil-in-water (o/w) emulsions upon aqueous dilution owing to the gentle agitation of the gastrointestinal fluids. The efficiency of oral absorption of the drug compound from the SEDDS depends on many formulation-related parameters, such as the formulations' components, polarity of the emulsion, droplet size and charge, all of which in essence determine the self-emulsification ability. Thus, only very specific pharmaceutical excipient combinations will lead to efficient self-emulsifying systems.

Methods for Administration and Treatment with Amphotericin B

The administration of intravenous AmpB has been limited by its dose-dependent kidney toxicity that has not been predictable by monitoring plasma and/or serum drug concentration. A number of studies have reported that AmpB, solubilized in methanol, is poorly absorbed from the gastrointestinal (GI) tract and therefore is not commonly administered orally but intravenously, which can result in the aforementioned renal toxicity. However, to date, few studies investigating the development and assessing the antifungal activity of oral AmpB formulations have been reported.

In another aspect, the invention provides a method for treating an infectious disease treatable by the administration of amphotericin B. In the method, a therapeutically effective amount of an amphotericin B formulation of the invention is administered to a subject in need thereof. In one embodiment, the formulation is administered orally. In another embodiment, the formulation is administered topically.

As used herein, the terms "treating" and "treatment" refer to reduction in severity and/or frequency of symptoms, elimination of symptoms and/or underlying cause, reduction in likelihood of the occurrence of symptoms and/or underlying cause, and improvement or remediation of damage. Thus, "treating" a patient with an active agent as provided herein includes prevention of a particular condition, disease or disorder in a susceptible individual as well as treatment of a clinically symptomatic individual. As used herein, "effective amount" refers to an amount covering both therapeutically effective amounts and prophylactically effective amounts. As used herein, "therapeutically effective amount" refers to an amount that is effective to achieve the desired therapeutic result. A therapeutically effective amount of a given active agent will typically vary with respect to factors such as the type and severity of the disorder or disease being treated and the age, gender, and weight of the patient.

Infectious diseases treatable by the method and formulations of the invention include fungal infections (aspergillosis, blastomycosis, candidiasis, coccidioidomycosis, crytococcosis, histoplasmosis, mucormycosis, paracoccidioidomycosis, and sporotrichosis), visceral leishmaniasis, cutaneous leishmaniasis, Chagas disease, and Febrile neutropenia. Amphotericin B has been shown to bind to amyloid and prevent the formulation of fibrils. Amphotericin B has been indicated as useful for the treatment of Alzheimer's disease. Accordingly, the amphotericin B formulation of the invention can be used in the treatment of Alzheimer's disease.

In one embodiment, the invention provides a method for treating visceral leishmaniasis comprising orally administering an AmpB formulation of the invention to a subject in need thereof. In the method, a therapeutically effective amount of AmpB is administered to treat the condition. The therapeutically effective amount of AmpB administered can vary depending on the subject and the severity of the condition. In one embodiment, the therapeutically effective amount can range from about 0.1 to about 50 mg amphotericin B/kg subject body weight. In one embodiment, the effective amount is from about 1 about 25 mg amphotericin B/kg subject body weight. In another embodiment, the effective amount is from about 2.5 to about 10 mg amphotericin B/kg subject body weight.

The regiment for administration of AmpB can also vary depending on the subject and the severity of the condition. A dose of AmpB can be administered one or more times each day, for one or more days, which can be followed by a period of time (e.g., one or more days) during which no AmpB is administered, optionally followed by resumption of administration for a period of time (e.g., AmpB administered twice daily for five days, no administration for two days, followed by once daily administration for three days).

In one embodiment, from about 2.5 to about 10 mg amphotericin B/kg subject body weight is administered twice daily for five days.

In another embodiment, about 20 mg amphotericin B/kg subject body weight is administered once daily for five days.

In summary, in one aspect, the present invention provides amphotericin B formulations that can be orally administered. The amphotericin B formulations of the invention provide excellent drug solubilization, drug stability in simulated gastric and intestinal fluids, and have significant antifungal activity without the dose-limiting renal toxicity for which the parenteral formulations of amphotericin B are well known.

Therapeutic Agent Formulations

In another aspect, the present invention provides formulations for the delivery of therapeutic agents, methods for making the formulations, and methods for administering the therapeutic agents using the formulations.

In one aspect, the invention provides a formulation for the delivery of a therapeutic agent. The therapeutic agent formulation includes
 (a) a therapeutic agent;
 (b) one or more fatty acid glycerol esters;
 (c) one or more polyethylene oxide-containing fatty acid esters; and
 (d) optionally a tocopherol polyethylene glycol succinate.

In the therapeutic agent formulation above, the fatty acid glycerol esters, the polyethylene oxide-containing fatty acid esters, and the optional tocopherol polyethylene glycol succinate are as described above for the amphotericin B formulations. The amounts of these components in the above therapeutic agent formulation is also as described above for the amphotericin B formulations. The therapeutic agent can be present in the formulation in an amount from about 0.1 mg/mL to about 25 mg/mL of the formulation. In certain embodiments, the formulations can further include glycerol in an amount less than about 10% by weight. In one embodiment, the formulation includes a tocopherol polyethylene glycol succinate.

The therapeutic drug formulation of the invention advantageously solubilizes difficultly soluble therapeutic drugs. Representative therapeutic agents that can be advantageously formulated and delivered by the formulation and methods of the invention include anticancers, antibiotics, antiviral drugs, antimycotics, anti-prions, anti-amoebics, non-steroidal anti-inflammatory drugs, anti-allergics, immunosuppressive agents, coronary drugs, analgesics, local anesthetics, anxiolytics, sedatives, hypnotics, migraine relieving agents, drugs against motion sickness, and anti-emetics.

Specific therapeutic agents that can be advantageously formulated and delivered by the formulation and methods of the invention include tetracycline, doxycycline, oxytetracycline, chloramphenicol, erythromycin, acyclovir, idoxuridine, tromantadine, miconazole, ketoconazole, fluconazole, itraconazole, econazole, griseofulvin, amphotericin B, nystatine, metronidazole, metronidazole benzoate, tinidazole, indomethacin, ibuprofen, piroxicam, diclofenac, disodium cromoglycate, nitroglycerin, isosorbide dinitrate, verapamil, nifedipine, diltiazem, digoxine, morphine, cyclosporins, buprenorphine, lidocaine, diazepam, nitrazepam, flurazepam, estazolam, flunitrazepam, triazolam, alprazolam, midazolam, temazepam lormetazepam, brotizolam, clobazam, clonazepam, lorazepam, oxazepam, busiprone, sumatriptan, ergotamine derivatives, cinnarizine, anti-histamines, ondansetron, tropisetron, granisetrone, metoclopramide, disulfuram, vitamin K, paclitaxel, docetaxel, camptothecin, SN38, cisplatin, and carboplatin.

In certain embodiments, the therapeutic agent formulation of the invention can include a second therapeutic agent.

The therapeutic agent formulation can be a self-emulsifying drug delivery system.

In one embodiment, the therapeutic agent formulation includes
 (a) a therapeutic agent;
 (b) one or more fatty acid glycerol esters (e.g., oleic acid glycerol esters); and
 (c) optionally a tocopherol polyethylene glycol succinate (e.g., vitamin E TPGS).

In another embodiment, the therapeutic agent formulation includes
 (a) a therapeutic agent;
 (b) one or more fatty acid glycerol esters (e.g., oleic acid glycerol esters);
 (c) one or more polyethylene oxide-containing fatty acid esters (e.g., lauric, palmitic and/or stearic acid esters of polyethylene glycol); and
 (d) optionally a tocopherol polyethylene glycol succinate (e.g., vitamin E TPGS).

In one embodiment, the therapeutic agent formulation of the invention includes a therapeutic agent, PECEOL®, and GELUCIRE® 44/14. In another embodiment, the formulation includes a therapeutic agent, PECEOL®, and GELUCIRE® 50/13. In a further embodiment, the formulation includes a therapeutic agent, PECEOL®, and GELUCIRE® 53/10. In these embodiments, the ratio of PECEOL® to GELUCIRE® can be from 20:80 to 80:20 (e.g., 20:80, 30:70;

40:60; 50:50; 60:40; 70:30; and 80:20). In other embodiments, these formulations include a tocopherol polyethylene glycol succinate.

In another aspect, the invention provides a method for administering a therapeutic agent. In the method, a therapeutically effective amount of the therapeutic agent is administered using the therapeutic agent formulation described above. In one embodiment, the formulation is administered orally. In another embodiment, the formulation is administered topically.

In further aspects, the invention provides methods for treating conditions and diseases treatable by therapeutic agents formulated in accordance with the present invention. In the methods, an effective amount of a therapeutic drug formulation of the invention is administered to a subject in need thereof. The methods for treating conditions and diseases use formulations of the therapeutic agent families and specific therapeutic agents disclosed herein.

Therapeutic Drug Carrier

In a further aspect, the present invention provides compositions for formulating a therapeutic agent, methods for making the composition, and methods for formulating a therapeutic agent for delivery using the composition.

In one aspect, the invention provides a composition for formulating a therapeutic agent for delivery. The composition includes (a) one or more fatty acid glycerol esters;

(b) one or more polyethylene oxide-containing fatty acid esters; and (c) optionally a tocopherol polyethylene glycol succinate.

In the composition above, the fatty acid glycerol esters, the polyethylene oxide-containing fatty acid esters, and the tocopherol polyethylene glycol succinate are as described above for the amphotericin B formulations. The amounts of these components in the above composition are also as described above for the amphotericin B formulations. In certain embodiments, the compositions can further include glycerol in an amount less than about 10% by weight. In one embodiment, the composition includes a tocopherol polyethylene glycol succinate.

The composition advantageously solubilizes difficultly soluble therapeutic drugs for their delivery. With the incorporation of a therapeutic agent, the composition can provide a self-emulsifying drug delivery system.

In another embodiment, the composition includes (a) one or more fatty acid glycerol esters (e.g., oleic acid glycerol esters); and (b) one or more polyethylene oxide-containing fatty acid esters (e.g., lauric, palmitic and/or stearic acid esters of polyethylene glycol); and (c) optionally a tocopherol polyethylene glycol succinate (e.g., vitamin E TPGS).

In one embodiment, the composition includes PECEOL® and GELUCIRE® 44/14. In another embodiment, the composition includes PECEOL® and GELUCIRE® 50/13. In a further embodiment, the composition includes PECEOL® and GELUCIRE® 53/10. In these embodiments, the ratio of PECEOL® to GELUCIRE® can be from 20:80 to 80:20 (e.g., 20:80, 30:70; 40:60; 50:50; 60:40; 70:30; and 80:20). In certain embodiments, these compositions include a tocopherol polyethylene glycol succinate.

In another aspect, the invention provides a method for making a therapeutic agent formulation. In one embodiment of the method, a therapeutic agent is combined with the composition described above. In another embodiment of the method, a therapeutic agent is combined with one of the components of the composition (e.g., one or more fatty acid glycerol esters) to provide a first combination followed by combining the first combination with the other components of the composition (e.g., one or more polyethylene oxide-containing fatty acid esters). In one embodiment, the tocopherol polyethylene glycol succinate is included in the first combination. In another embodiment, the tocopherol polyethylene glycol succinate is added to the first combination.

The formulations and compositions of the invention described herein include (i.e., comprise) the components recited. In certain embodiments, the formulations and compositions of the invention include the recited components and other additional components that do not affect the characteristics of the formulations and compositions (i.e., the formulations and compositions consist essentially of the recited components). Additional components that affect the formulations' and compositions' characteristics include components such as additional therapeutic agents that disadvantageously alter or affect therapeutic profile and efficacy of the formulations or compositions, additional components that disadvantageously alter or affect the ability of the formulations and compositions to solubilize the recited therapeutic agent components, and additional components that disadvantageously alter or affect the ability of the formulations and compositions to increase the bioavailability of the recited therapeutic agent components. In other embodiments, the formulations and compositions of the invention include only (i.e., consist of) the recited components.

The formulations of the invention do not include poly (lactide-co-glycolide) (PLGA) and are not in the form of AmpB entrapped in PLGA nanoparticles.

The following examples are provide for the purpose of illustrating, not limiting, the invention.

EXAMPLES

Materials

The following materials were used as described in the following examples. Amphotericin B (from *Streptomyces* sp., *Calbiochem*, >80% purity) was purchased from Sigma (St. Louis, Mo.) and used without further purification. Poly(ethylene glycol)-lipids were all from Avanti Polar Lipids (Alabaster, Ala.). HPLC grade solvents were from Fluka. PECEOL® (glyceryl oleate) and GELUCIRE® 44/14 were obtained from Gattefossé Canada (Mississauga, Ontario). Simulated gastric fluid (SGF) without enzymes was composed of 30 mM NaCl, titrated to pH 1.2 with 1N HCl. Ethanol (100%) was purchased from Commercial Alcohols (Vancouver, BC). Mono- and di-glycerides were obtained from Gattefossé Canada (Toronto, ON, Canada). D-alpha-tocopheryl polyethylene glycol succinate (Vitamin E-TPGS; NF grade) was purchased from Eastman Chemical Co. (Kingsport, Tenn.). Methanol, HPLC water, acetonitrile and acetic acid were purchased from Fisher Scientific (Ottawa, ON Canada) and were of HPLC grade. Sodium chloride, hydrochloric acid, sodium hydroxide, dibasic potassium phosphate, sodium taurocholate and porcine pancreatin were purchased from Sigma Chemical Co. Egg phosphatidylcholine (lecithin) was purchased from Avanti Polar Lipids (Alabaster, Ala.). All other chemicals were of reagent grade purchased from Sigma-Aldrich.

Example 1

The Preparation of Representative Amphotericin B Formulations

In this example, the preparation of representative amphotericin formulations of the invention are described.

The preparation of two AmpB/TPGS formulations (AmpB/Peceol:Gelucire 44-14 (50:50 and 60:40)+5% v/v vitamin E-TPGS) are described.

Concurrent to making the AmpB in 50:50 and 60:40 Peceol/Gelucire 44-14+5% v/v vitamin E-TPGS vehicles, a single preparation each of 50:50 and 60:40 Peceol/Gelucire 44-14+5% v/v vitamin E-TPGS vehicles without AmpB were prepared.

Two formulations of the AmpB in 50:50 Peceol/Gelucire 44-14+5% v/v vitamin E-TPGS were prepared. For each preparation, 100 mg of AmpB (80%, Sigma) was measured into a 100 mL foil-wrapped round-bottomed flask. To this was added 50 mL of 100% ethanol (EtOH). The flask was attached to a rotary-evaporator and mixed for 30 min with rotation while incubated in a water bath at 48° C. Peceol (Gattéfossé), Gelucire 44-14 (Gattéfossé), and vitamin E-TPGS (Eastman) were warmed in a 49° C. water bath for 30 mins. After 30 mins of mixing, the AmpB-EtOH mixture, 9.5 mL Peceol, 9.5 mL Gelucire 44-14, and 1 mL vitamin E-TPGS (5% of total volume of 20 mL) were added to the round-bottomed flask. Mixing continued at 48° C. for 1 hr. After 1 hr of mixing, ethanol was removed by evaporation. The product was transferred to a foil-wrapped conical screw-cap tube with the head-space flushed with nitrogen. After capping, the vial was sealed with PARAFILM wax and stored at 4° C. for further temperature and fsSGF stability studies.

Two formulations of AmpB/60:40 Peceol/Gelucire 44-14+5% v/v vitamin E-TPGS were similarly prepared.

Standard curves were developed for use in determining the concentration of AmpB in each formulation after incubation at 4° C., RT, and 43° C. Blanks were prepared by diluting 40 µL of each vehicle formulation in 1960 µL methanol. 1600 µL of this dilution was then diluted in 78.4 mL methanol for a total volume of 80 mL of blank diluted at 1:5000. 1 mg AmpB was then diluted in 10 mL of blank diluted at 1:5000. The dilution was warmed and stirred in a water bath at 48° C.

AmpB in Peceol was prepared as follows: 100 mg AmpB (80%, Sigma) was added to a 100 mL foil-wrapped round-bottomed flask. 20 mL of Peceol was then added and the mixture was incubated in a rotary-evaporator in a water bath at 43° C. for 2 hrs. The product was then transferred to a 50 mL foil-wrapped conical screw-cap vial with the head-space flushed with nitrogen gas. After capping, the vial was sealed with paraffin wax and stored at 4° C. for further temperature stability studies.

Example 2

The Temperature Stability of Representative Amphotericin B Formulations

In this example, the temperature stability of the two AmpB/TPGS formulations (AmpB/Peceol:Gelucire 44-14 (50:50 and 60:40)+5% v/v vitamin E-TPGS), prepared as described in Example 1, are compared to that of an AmpB/Peceol formulation.

Three formulations of AmpB were prepared. Each formulation was aliquoted and stored at three temperatures, 4° C., room temperature (RT, ranging between 23° to 30° C.), and 43° C. for time periods ranging from 0 days of incubation to 60 days of incubation. At specified time points over 39 days samples of each formulation at each temperature was diluted in methanol to fully solubilize the AmpB. The absorbance of AmpB was measured using the UV-Vis spectrophotometry (407 nm) using a background containing the lipid vehicles alone at the same dilution and compared to a standard curve prepared with the corresponding lipid vehicles. The concentration of AmpB in the samples was calculated and compared to the original concentration of AmpB in the formulations, expressed as a mean percentage (+/−SD, n=3).

The following time points were evaluated: 0, 2, 3, 7, 10, 14, 17, 21, 28, 35, 40, 50, and 60 days (12 time-points, 3 replicates, 3 temperatures and 3 formulations). The formulations were warmed in an Environ Shaker (Lab line model) for 1 hr at 48° C. (48° C. was chosen as the warming temperature as it is below the temperature at which degradation of the components begins and it is above the melting temperature of all the vehicle components (44° C.)). Once the formulations were melted, they were mixed using a Barnstead Thermolyne Shaker/Rotisserie, Labquake model, while maintaining the temperature at 48° C. in the Environ Shaker. Formulations were transferred to the water bath (48° C.) and remained in the water bath for the duration of aliquoting.

100 µL from the AmpB in Peceol, AmpB/50:50 Peceol/Gelucire 44-14+5% v/v vitamin E-TPGS formulation, and AmpB/60:40 Peceol/Gelucire 44-14+5% v/v vitamin E-TPGS were aliquoted into microcentrifuge tubes, n=3. Each aliquoted sample was head capped with nitrogen gas and sealed with paraffin wax. Samples stored at 4° C. were stored in a refrigerator; room temperature (RT) samples were stored at Ambient room temperature (23° C.); and samples stored at 43° C. were stored in a Boekel Scientific Incubator model 133000.

At each time point the sample was removed from incubation and transferred for evaluation. The samples were wrapped in aluminum foil and warmed in the Environ Shaker at 48° C. for 1 hr. Each sample was mixed prior to dilution until the sample was uniform in appearance. Samples were vortexed for 2 min to provide apparently homogenous and monophasic samples. 20 µL of sample was diluted with 1980 µL methanol for a first dilution of 1:100. A second dilution of 1:50 was conducted by diluting 40 µL of the first dilution 1960 µL methanol. A final dilution of 1:5000 was obtained for each sample. The absorbance of AmpB in each formulation incubated at either 4° C., RT, or 43° C. was determined using UV-Vis single-beam spectrophotometry (Varian Spectrophotometer, Cary Bio-100). Methanol served as the blank. Samples incubated at RT on time points day 2 and day 3 were assessed with a Unico 2800 UV/Vis spectrophotometer. The absorbance value was compared to a standard curve and the concentration of the sample calculated. The concentrations were compared as a % of the original concentration measured on day 0.

The results for the two TPGS-containing AmpB formulations are compared to the non-TPGS-containing AmpB formulations in FIGS. 2A-2C.

Example 3 fsSGF Stability of Representative Amphotericin B Formulations

In this example, the stability in fasted state simulated gastric fluid (fsSGF) of the two AmpB/TPGS formulations (AmpB/Peceol:Gelucire 44-14 (50:50 and 60:40)+5% v/v vitamin E-TPGS), prepared as described in Example 1, are compared.

AmpB in Peceol/Gelucire 44-14 (50:50 and 60:40)+5% v/v vitamin E-TPGS was incubated in 1:100 v/v fsSGF over a time of 2 hrs at 37° C. Samples were extracted from incubation media at periodic intervals. The concentration of AmpB was measured using UV-Vis spectrophotometry, compared to a standard curve containing the lipid vehicles and fsSGF at the appropriate dilution in methanol. The degradation of AmpB in the 50:50 Peceol/Gelucire 44-14/5% v/v vitamin E-TPGS vehicle was compared to the degradation of AmpB in the 60:40 Peceol/Gelucire 44-14/5% v/v vitamin E-TPGS.

Fasted state simulated gastric fluid (fsSGF) was prepared by reducing the pH of 30 mM NaCl to pH 1.2 using HCl. The AmpB formulations were melted in an Environ Shaker (Lab line model) at 48° C. and mixed using the Barnstead Thermolyne Shaker/Rotisserie (Labquake model) for 1 hr. Each vehicle, without AmpB, was warmed and mixed at the same time as the AmpB formulations. These vehicles were used in preparing blanks used in the spectrophotometer readings. As the formulations were melted, 8 foil-wrapped flasks with stir-bars were filled with 99 mL of fsSGF and warmed to 37° C. AmpB formulations were vortexed for 2 mins to mix thoroughly and then returned to the Environshaker to warm and rotate-mix. 1 mL of each AmpB formulation was transferred into the incubated fsSGF and stirred. 1 mL of each vehicle was transferred into the incubating fsSGF and stirred for 5 mins.

1 mL of fsSGF mixed with the AmpB formulations was withdrawn from incubation and prepared for absorbance readings at the following time points: 0 mins, 5 mins, 10 mins, 15 mins, 20 mins, 30 mins, 45 mins, 60 mins, 90 mins, and 120 mins (Varian Spectrophotometer, Cary Bio-100), n=3. Samples were prepared by diluting each 1 mL sample 1:10 in methanol and vortexed for 2 mins. A second dilution of 1:5 in methanol was made. The second dilution was likewise vortexed for 2 mins to ensure adequate mixing. The blank was prepared for spectrophotometer readings after 5 mins of incubation and were prepared in the same manner as the AmpB formulations. The blank was used to zero the UV-Vis spectrophotometer and absorbance measurements for AmpB were read at 407 nm. The absorbance readings of AmpB/Peceol/Gelucire 44-14 (50:50 and 60:40)+5% v/v vitamin E-TPGS formulations incubated in fsSGF were used to determine the concentration remaining in each formulation after the incubation times.

The concentration of AmpB in both the 50:50 and 60:40 Peceol/Gelucire 44-14+5% vitamin E-TPGS formulations remained high up to and including 45 mins of incubation in fsSGF warmed at 37° C. After 45 mins of incubation in fsSGF at 37° C. the amount of AmpB remaining in each AmpB formulation as a percentage of the original concentration was within 90% of the original concentration (FIG. 3). There was a rapid decline between the 45 min and 90 min time points for both formulations. There was no statistical difference between either formulation with regard to the percent concentration of AmpB remaining following incubation at the various time points.

Example 4

Emulsion Droplet Size and Distribution of Representative Amphotericin B Formulations In this example, the emulsion droplet size and distribution of two representative AmpB/TPGS formulations of the invention (AmpB/Peceol/Gelucire (50:50 and 60:40) 44-14+5% v/v vitamin E-TPGS), prepared as described in Example 1, are compared after incubation in fasted state simulated gastric fluid (fsSGF) at 37° C.

Emulsified droplet size of AmpB in 50:50 Peceol/Gelucire 44-14/5% v/v vitamin E-TPGS and AmpB in 60:40 Peceol/Gelucire 44-14/5% v/v vitamin E-TPGS after incubation in fsSGF was evaluated concurrently with the stability in fsSGF study described above. Samples were extracted from the incubation medium after 30 mins, 60 mins, and 120 mins. Droplet sizes for AmpB in each vehicle formulation were determined using a particle-sizer (Malvern Zetasizer 3000 HS) at 37° C. Size distribution was also determined.

The emulsion droplet size results are presented in FIG. 4. Referring to FIG. 4, the emulsion droplet size of either formulation is similar for at least the first 60 mins incubation. Following 120 mins incubation, the emulsion droplet size for the AmpB/50:50 Peceol/Gelucire 44-14+5% v/v vitamin E-TPGS reduced to less than 200 nm. This is in contrast to the emulsion droplet size of the AmpB/60:40 Peceol/Gelucire 44-14+5% v/v vitamin E-TPGS, which remained at slightly more than 400 nm. The droplet size distribution indicated that the formulations were substantially homogenous.

Example 5

Amphotericin B Concentration by High Performance Liquid Chromatography

The HPLC column was a BDS Hypersil C18, 5 μm, 250× 4.6 mm (Thermo Scientific, Waltham, Mass.), with a C18 guard column from Phenomenex (Torrance, Calif.). During sample runs, the column incubator was set to 40° C. The mobile phase consisted of acetonitrile:acetic acid:water in a ratio of 57:4.3:38.7 (v/v/v). The injection volume was 90 μL and the flow rate was 0.8 mL/min with a run time of 20 min. The retention time of AmpB under these conditions was 15 min. Six triplicate standards of AmpB in methanol:water (50:50 v/v) were used for external calibration, with a linear range of 31.25-1000 ng/mL by linear regression analysis ($r^2 > 0.999$). For analysis of AmpB in lipid formulations, the samples were warmed in a 48° C. water bath to melt the lipids, followed by vigorous vortexing for 2 min. A double dilution was then used. With a micropipettor, 100 μL were transferred to a glass vial followed by the addition of 9.9 mL methanol and vortexing for 1 min. From this dilution, 100 μL was aliquoted to another glass vial, followed by addition of 9.9 mL of methanol:water (50:50 v/v) and vortexed for 1 min, thereby making 1:10,000 dilutions of the original samples. These final dilutions were analyzed by HPLC as described above and compared to the standard curve for quantification of AmpB concentration.

Example 6

Amphotericin B Formulation Stability at 30° and 43° C.

The stability testing of AmpB in each of the four oral lipid formulations (AmpB in mono- and di-glycerides with or without vitamin E-TPGS) was performed at 30° C. and 43° C. at ambient humidity (>85%). For stability analysis at 30° C., 18 time points covering a 12 month period were chosen. For 43° C., 12 time points covering a 6 month period were chosen. Four independent replicate samples were prepared for each time point by melting the batch of AmpB in lipids at 48° C. and stirring to homogeneity, followed by quickly aliquoting 0.5 mL of the AmpB/lipid mixture into individual polypropylene microcentrifuge tubes. The tubes were then sealed with parafilm. Samples were protected from light with foil and stored in incubators at 30° or 48° C. The starting concentration of AmpB in the lipids was measured by HPLC (3-4 mg/mL depending on batch concentration). All subsequent measurements of AmpB during the course of the stability study were performed by HPLC as described above and are reported as "% of original concentration" as measured on the day the sample was aliquoted (day 0). The rate of loss of AmpB per day was calculated as: ($[AmpB]_{day\ 0}$−$[AmpB]_{day\ 60}$/60 days.=µg/mL day loss. These data are reported as mean±SD for 4 independent replicates. Statistical differences were assessed pair-wise by Student's t test (paired, 2-tailed) (SigmaStat v.3.5) with significance set at p<0.05.

Example 7

Amphotericin B Formulation Stability in Simulated Gastric Fluid (SGF) and Fasted-State Intestinal Fluid (FaSSIF)

Simulated Gastric Fluid was prepared as per United States Pharmacopeia (USP V.28): 30 mM sodium chloride, with pH adjusted to 1.2 with hydrochloric acid. Fasted-State Simulated Intestinal Fluid without enzymes was also prepared according to the USP V.28 and was composed of 3.9 g/L dibasic potassium phosphate, 1.613 g/L sodium taurocholate (=3 mM), lecithin (egg phosphatidylcholine) 0.57 g/L (=0.75 mM), potassium chloride 7.7 g/L dissolved in water and with sufficient hydrochloric acid to adjust the pH to 6.5.

AmpB formulations in mono- and di-glycerides with or without Vitamin E-TPGS and the corresponding drug-free vehicle controls were melted at 48° C. in a water bath followed by vigorous vortexing for 2 min. SGF or FaSSIF was warmed to 37° C. in 3 foil-wrapped 500 mL beakers on stirring hotplates. For incubation in SGF, samples (1 mL) were added to 99 mL of SGF (1:100 v/v dilution). For incubation in FaSSIF, samples (0.5 mL) were added to 249.5 mL FaSSIF to achieve a dilution of 1:500 v/v. The samples were mixed vigorously at 37° C. over 2 h for SGF incubation and over 4 h for FaSSIF incubation, producing an emulsified mixture. At 0, 10, 30, 45, 60, 90, 120 min for both fluids and additionally for 240 min for samples in FaSSIF, triplicate 1 mL samples were withdrawn from the beakers while the mixing continued. The 1 mL samples were diluted with 9 mL methanol and vortexed to clarity. Quantification of AmpB concentration was performed by ultraviolet spectroscopy ($\lambda$=407) on a Carey Bio-300 UV-visible spectrophotometer (Varian Canada, Mississauga, Ontario) by comparison to an external standard curve consisting of UV measurements of AmpB in methanol containing the same dilution of the corresponding vehicle control for each formulation type. The linear range by regression analysis was 0.5-1.75 µg/mL ($r^2$>0.999).

Example 8

Amphotericin B Formulation Emulsion Droplet Sizing in Simulated Gastric and Simulated Fasted-State Intestinal Fluid The translucent emulsion formed during incubation of AmpB in oral lipids in simulated gastric or intestinal fluid tends to cream (oil to the top of the aqueous phase) if not continuously mixed. Therefore, 1 mL samples were obtained mid-beaker depth at 0.5, 1 and 2 h for SGF incubations and at 2 h and 4 h for FaSSIF incubations during vigorous mixing and transferred to a plastic cuvette. Samples were mixed again by vortexing prior to placement in the sizing instrument. The emulsion droplet size was measured by dynamic light scattering (Malvern Zetasizer, Malvern Instruments, Worchestershire, UK) operating with an argon laser ($\lambda$=633 nm) and with the sample holder kept at 37° C. for 3 runs of 1 minute each, during which time the measurements were stable. Intensity weighting was used. Data are reported as the mean droplet diameter±standard deviation (SD) from mean of 3 separate samples, where three runs were averaged for each sample.

Example 9

Effectiveness of a Representative Amphotericin B Formulation in a Visceral Leishmaniasis-infected Murine Model To determine the anti-leishmanial activity of a representative oral AmpB formulation, the following studies were completed. BALB/c mice were intravenously infected with $5\times10^7$ Leishmania donovani LV82 promastigotes (obtained by culturing amastigotes taken directly from the spleen of an infected hamster) seven days prior to treatment. Following the seven days, mice were either administered five daily doses of miltefosine at 3 mg/kg po, or Formulation A at 2.5, 5, and 10 mg/kg po bid for five consecutive days or 20 mg/kg po qd for five consecutive days. Appropriate vehicle controls were also assessed. Animals were sacrificed 14 days post infection and Leishman-Donovan units (LDU) were assessed in livers of mice post mortem via microscopic enumeration of Giemsa-stained liver smears Results for Formulation A compared to water control, vehicle control, and miltefosine are set forth below.

TABLE 3

Dosing Summary

| Group | BALB/c Mice No. | No. of LV82 PM | Body Weight (g) | Dose |
|---|---|---|---|---|
| Group A | 1 | $5 \times 10^7$/ | 18.2 | ddH$_2$O |
| Water | 2 | mouse i.v. | 19.3 | 100 ul/Mouse p.o. qd |
| Control | 3 | | 17.6 | |
| p.o. qd | 4 | | 16.5 | |
| Group B | 1 | $5 \times 10^7$/ | 19.1 | Vehicle |
| Vehicle | 2 | mouse i.v. | 17.3 | 100 ul/mouse p.o. bid |
| Control | 3 | | 19.0 | |
| p.o. qd | 4 | | 19.7 | |
| Group C | 1 | $5 \times 10^7$/ | 20 | 0.6 mg/ml, 100ul/Mouse |
| Miltefosine | 2 | mouse i.v. | 18.2 | 0.6 mg/ml, 90 ul/Mouse |
| 3 mg/kg | 3 | | 20.4 | 0.6 mg/ml, 100ul/Mouse |
| p.o. qd | 4 | | 18.4 | 0.6 mg/ml, 90 ul/Mouse |
| Group D | 1 | $5 \times 10^7$/ | 16.4 | 3.94 mg/ml, 10 ul/Mouse |
| 2.5 mg/kg | 2 | mouse i.v. | 18.5 | 3.94 mg/ml, 10 ul/Mouse |
| p.o. qd | 3 | | 19.8 | 3.94 mg/ml, 15 ul/Mouse |
| | 4 | | 20.3 | 3.94 mg/ml, 15 ul/Mouse |
| Group E | 1 | $5 \times 10^7$/ | 20.2 | 3.94 mg/ml, 25 ul/Mouse |
| 5 mg/kg | 2 | mouse i.v. | 19 | 3.94 mg/ml, 25 ul/Mouse |
| p.o. qd | 3 | | 16.7 | 3.94 mg/ml, 20 ul/Mouse |
| | 4 | | 16.8 | 3.94 mg/ml, 20 ul/Mouse |
| Group F | 1 | $5 \times 10^7$/ | 20.3 | 3.94 mg/ml, 50 ul/Mouse |
| 10 mg/kg | 2 | mouse i.v. | 18.2 | 3.94 mg/ml, 45 ul/Mouse |
| p.o. qd | 3 | | 17.0 | 3.94 mg/ml, 45 ul/Mouse |
| | 4 | | 16.1 | 3.94 mg/ml, 40 ul/Mouse |
| Group G | 1 | $5 \times 10^7$/ | 17.8 | 3.94 mg/ml, 90 ul/Mouse |
| 20 mg/kg | 2 | mouse i.v. | 20.4 | 3.94 mg/ml, 100ul/Mouse |
| p.o. qd | 3 | | 18.9 | 3.94 mg/ml, 100ul/Mouse |
| | 4 | | 17.9 | 3.94 mg/ml, 90 ul/Mouse |

TABLE 4

Murine VL model in vivo efficacy for Formulation A compared controls and miltefosine: LDU Results.

| Group | Mice No. | Body Weight (g) | Liver weight (g) | Spleen Weight (g) | # of amastigotes per 200 nuclei | LDU | LDU mean ± SD |
|---|---|---|---|---|---|---|---|
| Group A | 1 | 18.4 | 0.9763 | 0.1209 | 639 | 3119.279 | 3031.263 ± |
| Water | 2 | 19.6 | 1.0948 | 0.1122 | 545 | 2983.33 | 139.644 |
| Control | 3 | 18.3 | 1.0749 | 0.1207 | 589 | 3165.581 | |
| p.o. qd | 4 | 17.1 | 1.0295 | 0.1101 | 555 | 2856.863 | |
| Group B | 1 | 19.2 | 1.0545 | 0.1289 | 637 | 3358.583 | 3183.561 ± |
| Vehicle | 2 | 17.9 | 0.9648 | 0.1148 | 526 | 2537.424 | 446.123 |
| Control | 3 | 19.2 | 1.0956 | 0.1153 | 599 | 3281.322 | |
| p.o. qd | 4 | 20.1 | 1.3029 | 0.1266 | 546 | 3556.917 | |
| Group C | 1 | 19.8 | 1.1060 | 0.1152 | 286 | 1581.58 | 1537.604 ± |
| Miltefosine | 2 | 18.8 | 1.0114 | 0.1265 | 283 | 1431.131 | 154.615 |
| 3 mg/kg | 3 | 19.8 | 1.1541 | 0.1216 | 301 | 1736.921 | |
| p.o. qd | 4 | 18.5 | 1.0693 | 0.1053 | 262 | 1400.783 | |
| Group D | 1 | 16.3 | 0.9053 | 0.1232 | 340 | 1539.01 | 1938.827 ± |
| 2.5 mg/kg | 2 | 18.5 | 0.9572 | 0.1111 | 419 | 2005.334 | 276.826 |
| p.o. qd | 3 | 20.1 | 1.1366 | 0.1291 | 358 | 2034.514 | |
|  | 4 | 20.1 | 1.1020 | 0.1211 | 395 | 2176.45 | |
| Group E | 1 | 20.2 | 1.0398 | 0.123 | 291 | 1512.909 | 1407.452 ± |
| 5 mg/kg | 2 | 18.2 | 0.9404 | 0.118 | 295 | 1387.09 | 98.09 |
| p.o. qd | 3 | 17.6 | 0.9221 | 0.0992 | 314 | 1447.697 | |
|  | 4 | 17 | 0.9568 | 0.1192 | 268 | 1282.112 | |
| Group F | 1 | 20.0 | 1.1404 | 0.1163 | 247 | 1180.314 | 954.073 ± |
| 10 mg/kg | 2 | 17.5 | 0.9145 | 0.1146 | 210 | 960.225 | 161.491 |
| p.o. qd | 3 | 17.7 | 0.9387 | 0.1148 | 178 | 835.443 | |
|  | 4 | 15.7 | 0.8663 | 0.1141 | 194 | 840.311 | |
| Group G | 1 | 17.9 | 0.8902 | 0.1132 | 124 | 551.924 | 557.506 ± |
| 20 mg/kg | 2 | 20.0 | 1.0937 | 0.1205 | 109 | 596.0665 | 35.296 |
| p.o. qd | 3 | 18.7 | 1.1132 | 0.1263 | 92 | 512.072 | |
|  | 4 | 18.1 | 1.0754 | 0.1028 | 106 | 569.962 | |

TABLE 5

Murine VL model in vivo efficacy for Formulation A compared controls and miltefosine: Body Weight.

| Group | Mean Body Weight Pre-treatment | Mean Body Weight Post-treatment |
|---|---|---|
| Water Control p.o. qd | 17.9 | 18.4 |
| Vehicle Control p.o. qd | 18.8 | 19.1 |
| Miltefosine 3 mg/kg, p.o. qd | 19.3 | 19.2 |
| Formulation A 2.5 mg/kg, p.o. qd | 18.8 | 18.8 |
| Formulation A 5 mg/kg, p.o. qd | 18.2 | 18.3 |
| Formulation A 10 mg/kg, p.o. qd | 17.9 | 17.7 |
| Formulation A 20 mg/kg, p.o. qd | 18.8 | 18.7 |

TABLE 6

Murine VL model in vivo efficacy for Formulation A compared controls and miltefosine: % Inhibition (water control).

| Group | % Reduction compared to water control (Average) | SD |
|---|---|---|
| Water Control p.o. qd | 0 | 0 |
| Vehicle Control p.o. qd | −5.0 | 14.7 |
| Miltefosine 3 mg/kg, p.o. qd | 49.3 | 5.1 |
| Formulation A 2.5 mg/kg, p.o. qd | 38.8 | 9.1 |
| Formulation A 5 mg/kg, p.o. qd | 53.6 | 3.2 |
| Formulation A 10 mg/kg, p.o. qd | 68.5 | 5.3 |
| Formulation A 20 mg/kg, p.o. qd | 81.6 | 1.1 |

TABLE 7

Murine VL model in vivo efficacy for Formulation A compared controls and miltefosine: % Inhibition (vehicle control).

| Group | % Reduction compared to Vehicle control (Average) | SD |
|---|---|---|
| Vehicle Control p.o. qd | 0 | 0 |
| Miltefosine 3 mg/kg, p.o. qd | 51.7 | 4.9 |
| Formulation A 2.5 mg/kg, p.o. qd | 39.1 | 8.7 |
| Formulation A 5 mg/kg, p.o. qd | 55.8 | 3.1 |
| Formulation A 10 mg/kg, p.o. qd | 70.0 | 5.1 |
| Formulation A 20 mg/kg, p.o. qd | 82.5 | 1.1 |

While illustrative embodiments have been illustrated and described, it will be appreciated that various changes can be made therein without departing from the spirit and scope of the invention.

The embodiments of the invention in which an exclusive property or privilege is claimed are defined a follows:

1. An amphotericin B formulation, comprising,
   (a) amphotericin B;
   (b) one or more fatty acid glycerol esters; and
   (c) one or more polyethylene oxide-containing fatty acid esters; and
   (d) a tocopherol polyethylene glycol succinate.

2. The formulation of claim 1, wherein amphotericin B is present in the formulation in an amount from about 0.5 to about 10 mg/mL of the formulation.

3. The formulation of claim 1, wherein the polyethylene oxide-containing fatty acid esters comprise a polyethylene oxide ester of a C8-C22 saturated fatty acid.

4. The formulation of claim 1, wherein the polyethylene oxide-containing fatty acid esters comprise a polyethylene oxide having an average molecular weight of from about 750 to about 2000.

5. The formulation of claim 1, wherein the ratio of the fatty acid glycerol esters to polyethylene oxide-containing fatty acid esters is about 60:40 v/v or about 50:50 v/v.

6. The formulation of claim 1, wherein the tocopherol polyethylene glycol succinate is a vitamin E tocopherol polyethylene glycol succinate.

7. The formulation of claim 1, wherein the tocopherol polyethylene glycol succinate is present in the formulation in an amount from about 0.1 to about 10 percent by volume based on the total volume of the formulation.

8. The formulation of claim 1, wherein the formulation is a self-emulsifying drug delivery system.

9. A method for administering amphotericin B, comprising administering a formulation of claim 1 to a subject in need thereof.

10. The method of claim 9, wherein the formulation is administered orally.

11. The method of claim 10, wherein the formulation is administered topically.

12. A method for treating an infectious disease treatable by the administration of amphotericin B, comprising administering to a subject in need thereof a therapeutically effective amount of an amphotericin B formulation of claim 1.

13. The method of claim 12, wherein the formulation is administered orally.

14. The method of claim 12, wherein the formulation is administered topically.

15. The method of claim 12, wherein the infectious disease is a fungal infection, visceral leishmaniasis, cutaneous leishmaniasis, Chagas disease, or Febrile neutropenia.

16. The method of claim 15, wherein the fungal infection is aspergillosis, blastomycosis, candidiasis, coccidioidomycosis, crytococcosis, histoplasmosis, mucormycosis, paracoccidioidomycosis, or sporotrichosis.

17. The formulation of claim 1, wherein the ratio of the fatty acid glycerol esters to polyethylene oxide-containing fatty acid esters is from about 20:80 to about 80:20 v/v.

* * * * *